(12) United States Patent
Billedeau

(10) Patent No.: US 8,361,962 B2
(45) Date of Patent: Jan. 29, 2013

(54) TRICYCLIC INHIBITORS OF JAK

(75) Inventor: Roland Joseph Billedeau, Santa Clara, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 12/825,390

(22) Filed: Jun. 29, 2010

(65) Prior Publication Data

US 2011/0021425 A1    Jan. 27, 2011

Related U.S. Application Data

(60) Provisional application No. 61/228,816, filed on Jul. 27, 2009.

(51) Int. Cl.
*A61K 38/18* (2006.01)
*A61K 31/541* (2006.01)
*A61K 31/4985* (2006.01)
*A61P 19/02* (2006.01)
*A61P 29/00* (2006.01)
*C07D 279/12* (2006.01)
*C07D 487/14* (2006.01)

(52) U.S. Cl. ..... 514/8.4; 514/228.5; 514/250; 544/58.2; 544/346

(58) Field of Classification Search ................. 514/8.4, 514/228.5, 250; 544/58.2, 346
See application file for complete search history.

(56) References Cited

U.S. PATENT DOCUMENTS 6,235,740 B1    5/2001    Barrish et al.
2009/0312338 A1*    12/2009    Wishart et al. ................ 514/250

FOREIGN PATENT DOCUMENTS

| WO | 99/45009 | 9/1999 |
|---|---|---|
| WO | 2008/079965 | 7/2008 |
| WO | 2009/152133 | 12/2009 |

OTHER PUBLICATIONS

Annu. Rev. Immunol. 16 (1998) pp. 293-322.
Leonard et al., (2000) J. Allergy Clin. Immunol. 105:877-888.
Oncogene 19 (2000) pp. 5662-5679.
Demoulin et al., (1996) Mol. Cell. Biol. 16:4710-6.
Jurlander et al. (1997) Blood 89:4146-52.
Kaneko et al. (1997) Clin. Exp. Immun. 109:185-193.
Nakamura et al., (1996) J. Biol. Chem. 271:19483-8.
Kudlacz et al., (2004) Am. J. Transplant 4:51-57.
Changelian (2003) Science 302:875-878.
Suzuki et al., (2000) Blood 96:2172-2180.
Malaviya et al., (1999) Biochem. Biophys. Res. Commun. 257:807-813.
Malaviya et al. (1999) J. Biol. Chem. 274:27028-27038.
Kirken (2001) Transpl. Proc. 33:3268-3270.
Muller-Ladner et al., (2000) J. Immunol. 164:3894-3901.
Trieu et al., (2000) Biochem. Biophys. Res. Commun. 267:22-25.
Sudbeck et al. (1999) Clin. Cancer Res. 5:1569-1582.
Nielsen et al. (1997) Prac. Natl. Acad. Sci. USA 94:6764-6769.
Yu et al. (1997) J. Immunol. 159:5206-5210.
Catlett-Falcone et al. (1999) Immunity 10:105-115.
J. Immunol. 168 (2002) pp. 2475-2482.
Blood 103 (2004) pp. 2009-2018.
J. Investig. Med. 44 (1996) pp. 304-311.
Curr. Opin. Cell Biol. 9 (1997) pp. 233-239.
International Search Report in Ref. 26219 WO dated Sep. 30, 2010.

* cited by examiner

*Primary Examiner* — Yong Chu
(74) *Attorney, Agent, or Firm* — George W. Johnston; Dennis P. Tramaloni; Jennifer L. Kisko

(57) ABSTRACT

The present invention relates to the use of novel compounds of Formulae I-II,

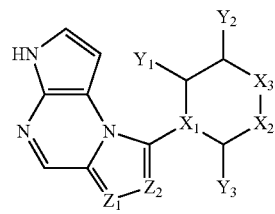

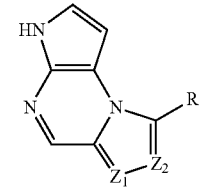

wherein the variables R, $X^1$, $X^2$, $X^3$, $Y^1$, $Y^2$, $Y^3$, $Z^1$, and $Z^2$ are defined as described herein, which inhibit JAK and are useful for the treatment of auto-immune and inflammatory diseases.

19 Claims, No Drawings

TRICYCLIC INHIBITORS OF JAK

CROSS-REFERENCE TO RELATED APPLICATIONS

This application is entitled to the benefit of U.S. provisional patent application Ser. No. 61/228,816 filed on Jul. 27, 2009,the disclosure of which is incorporated herein by reference.

SEQUENCE LISTING

The instant application contains a Sequence Listing which has been submitted in ASCII format via EFS-Web and is hereby incorporated by reference in its entirety. Said ASCII copy, created on Jul. 18, 2012 is named 26219.txt and is 424 bytes in size.

FIELD OF THE INVENTION

The present invention relates to the use of novel compounds which are JAK inhibitors and selectively inhibit JAK3 and are useful for the treatment of auto-immune and inflammatory diseases.

BACKGROUND OF THE INVENTION

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

The JAKs (JAnus Kinases) are a family of cytoplasmic protein tyrosine kinases including JAK1,JAK2,JAK3 and TYK2. Each of the JAKs is preferentially associated with the intracytoplasmic portion of discrete cytokine receptors (*Annu. Rev. Immunol.* 16 (1998), pp. 293-322). The JAKs are activated following ligand binding and initiate signaling by phosphorylating cytokine receptors that, per se, are devoid of intrinsic kinase activity. This phosphorylation creates docking sites on the receptors for other molecules known as STAT proteins (signal transducers and activators of transcription) and the phosphorylated JAKs bind various STAT proteins. STAT proteins, or STATs, are DNA binding proteins activated by phosphorylation of tyrosine residues, and function both as signaling molecules and transcription factors and ultimately bind to specific DNA sequences present in the promoters of cytokine-responsive genes (Leonard et al., (2000), J. Allergy Clin. Immunol. 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas.

Thus, the JAKs and STATs are components of multiple potentially intertwined signal-transduction pathways (*Oncogene* 19 (2000), pp. 5662-5679), which indicates the difficulty of specifically targeting one element of the JAK-STAT pathway without interfering with other signal transduction pathways.

The JAK kinases, including JAK3,are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood. 89:4146-52; Kaneko et al., (1997), Clin. Exp. Immun. 109:185-193; and Nakamura et al.,(1996), J. Biol. Chem. 271: 19483-8). They are also known to be important to lymphocyte differentiation, function and survival. JAK3 in particular plays an essential role in the function of lymphocytes, macrophages, and mast cells. Given the importance of this JAK kinase, compounds which modulate the JAK pathway, including those selective for JAK3,can be useful for treating diseases or conditions where the function of lymphocytes, macrophages, or mast cells is involved (Kudlacz et al., (2004) Am. J. Transplant 4:51-57; Changelian (2003) Science 302:875-878). Conditions in which targeting of the JAK pathway or modulation of the JAK kinases, particularly JAK3,are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes), and inflammation (e.g., asthma, allergic reactions). Conditions which can benefit from inhibition of JAK3 are discussed in greater detail below.

However, in contrast to the relatively ubiquitous expression of JAK1,JAK2 and Tyk2, JAK3 has a more restricted and regulated expression. Whereas some JAKs (JAK1,JAK2, Tyk2) are used by a variety of cytokine receptors, JAK3 is used only by cytokines that contain a yc in their receptor. JAK3,therefore, plays a role in cytokine signaling for cytokines which receptor was shown to date to use the common gamma chain; IL-2,IL-4,IL-7,IL-9,IL-15 and IL-21. JAK1 interacts with, among others, the receptors for cytokines IL-2, IL-4,IL-7,IL-9 and IL-21, while JAK2 interacts with, among others, the receptors for IL-9 and TNF-alpha. Upon the binding of certain cytokines to their receptors (e.g., IL-2,IL-4,IL-7,IL-9,IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as transplant rejection and autoimmune diseases.

In particular, JAK3 has been implicated in a variety of biological processes. For example, the proliferation and survival of murine mast cells induced by IL-4 and IL-9 have been shown to be dependent on JAK3- and gamma chain-signaling (Suzuki et al., (2000), Blood 96:2172-2180). JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunal. 164:3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad. Sci. USA 94:6764-6769); and abnormal cell growth (Yu et al., (1997), J. Immunol. 159:5206-5210; Catlett-Falcone et al., (1999), Immunity 10:105-115).

JAK3 inhibitors are useful therapy as immunosuppressive agents for organ transplants, xeno transplantation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

Non-hematopoietic expression of JAK3 has also been reported, although the functional significance of this has yet to be clarified (*J. Immunol.* 168 (2002), pp. 2475-2482). Because bone marrow transplants for SCID are curative (*Blood* 103 (2004), pp. 2009-2018), it seems unlikely that JAK3 has essential non-redundant functions in other tissues or organs. Hence, in contrast with other targets of immunosuppressive drugs, the restricted distribution of JAK3 is appealing. Agents that act on molecular targets with expression limited to the immune system might lead to an optimal efficacy:toxicity ratio. Targeting JAK3 would, therefore, theoretically offer immune suppression where it is needed (i.e. on cells actively participating in immune responses) without resulting in any effects outside of these cell populations. Although defective immune responses have been described in various STAT$^{-/-}$ (*J. Investig. Med.* 44 (1996), pp. 304-311; *Curr. Opin. Cell Biol.* 9 (1997), pp. 233-239), the ubiquitous distribution of STATs and the fact that those molecules lack enzymatic activity that could be targeted with small-molecule inhibitors has contributed to their non-selection as key targets for immunosuppression.

In view of the numerous conditions that are contemplated to benefit by treatment involving modulation of the JAK pathways it is immediately apparent that new compounds that modulate JAK pathways and methods of using these compounds should provide substantial therapeutic benefits to a wide variety of patients. Provided herein are novel compounds for use in the treatment of conditions in which targeting of the JAK pathways or inhibition of JAK kinases, particularly JAK3,and are therapeutically useful for the treatment of auto-immune and inflammatory diseases.

SUMMARY OF THE INVENTION

The novel compounds provided herein selectively inhibit JAK3 and are useful for the treatment of auto-immune and inflammatory diseases. The compounds of the invention modulate the JAK pathways and are useful novel compounds for the treatment of auto-immune and inflammatory diseases, wherein preferred compounds selectively inhibit JAK3. For example, the compounds of the invention may inhibit JAK3, wherein preferred compounds are selective for JAK3 of the JAK kinases and are useful novel compounds for the treatment of auto-immune and inflammatory diseases. Furthermore, the compounds of the invention may inhibit JAK3 and JAK2,wherein preferred compounds are selective for JAK3 of the JAK kinases, and are useful novel compounds for the treatment of auto-immune and inflammatory diseases. Similarly, the compounds of the invention may inhibit JAK3 and JAK1,wherein preferred compounds are selective for JAK3 of the JAK kinases, and are useful novel compounds for the treatment of auto-immune and inflammatory diseases.

The present provides compounds of Formulae I-II,

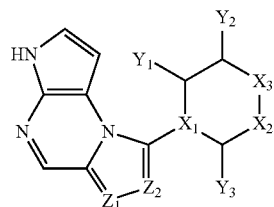

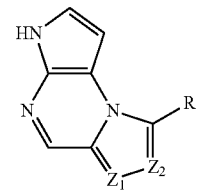

wherein the variables R, $X^1$, $X^2$, $X^3$, $Y^1$, $Y^2$, $Y^3$, $Z^1$, and $Z^2$ are defined as described herein, which inhibit JAK and are useful for the treatment of auto-immune and inflammatory diseases.

In one aspect, the application provides a method for treating an inflammatory and/or autoimmune condition comprising administering to a patient in need thereof a therapeutically effective amount of the compound of Formula I.

In one aspect, the application provides a method for treating an inflammatory and/or autoimmune condition comprising administering to a patient in need thereof a therapeutically effective amount of the compound of Formula II.

The application provides a pharmaceutical composition comprising the compound of Formula I, admixed with at least one pharmaceutically acceptable carrier, excipient or diluent.

The application provides a pharmaceutical composition comprising the compound of Formula II, admixed with at least one pharmaceutically acceptable carrier, excipient or diluent.

DETAILED DESCRIPTION OF THE INVENTION

The application provides a compound of Formula I

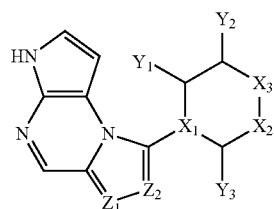

wherein:
$Z^1$ is CH or N;
$Z^2$ is CH or N;
$X^1$ is CH or N;
$X^2$ is $CH_2$, $NS(=O)_2R^1$, or $NC(=O)R^{1'}$;
$R^1$ is lower alkyl;
$R^{1'}$ is H, amino, or $R^{1''}$;

R$^{1''}$ is lower alkyl, optionally substituted with one or more R$^{1'''}$;
R$^{1'''}$ is halogen, lower alkoxy, cyano, or amino;
X$^3$ is CHR$^2$ or S(=O)$_2$;
R$^2$ is H or lower alkyl;
Y$^1$ is H, lower alkyl, lower alkoxy, halogen, or lower haloalkyl;
Y$^2$ is H or lower alkyl; and
Y$^3$ is H, lower alkyl, lower alkoxy, halogen, or lower haloalkyl;
or a pharmaceutically acceptable salt thereof.

In one variation of Formula I, Z$^1$ is CH and Z$^2$ is CH.
In one variation of Formula I, X$^1$ is CH.
In one variation of Formula I, X$^1$ is CH, Z$^1$ is CH, and Z$^2$ is CH.
In one variation of Formula I, X$^1$ is N.
In one variation of Formula I, X$^1$ is N, Z$^1$ is CH, and Z$^2$ is CH.
In one variation of Formula I, X$^3$ is S(=O)$_2$.
In one variation of Formula I, X$^3$ is S(=O)$_2$, X$^1$ is CH, Z$^1$ is CH, and Z$^2$ is CH.
In one variation of Formula I, X$^3$ is CH$_2$.
In one variation of Formula I, X$^3$ is CH$_2$, X$^1$ is CH, Z$^1$ is CH, and Z$^2$ is CH.
In one variation of Formula I, X$^2$ is NS(=O)$_2$CH$_2$CH$_3$.
In one variation of Formula I, X$^2$ is NS(=O)$_2$CH$_2$CH$_3$, X$^3$ is CH$_2$, X$^1$ is CH, Z$^1$ is CH, and Z$^2$ is CH.
In one variation of Formula I, Y$^2$ is H and Y$^3$ is H.
In one variation of Formula I, Y$^2$ is H and Y$^3$ is H, X$^2$ is NS(=O)$_2$CH$_2$CH$_3$, X$^3$ is CH$_2$, X$^1$ is CH, Z$^1$ is CH, and Z$^2$ is CH.
In one variation of Formula I, wherein Y$^1$ is methyl.
In one variation of Formula I, wherein Y$^1$ is methyl, Y$^2$ is H and Y$^3$ is H, X$^2$ is NS(=O)$_2$CH$_2$CH$_3$, X$^3$ is CH$_2$, X$^1$ is CH, Z$^1$ is CH, and Z$^2$ is CH.
In one variation of Formula I, Z$^1$ is N and Z$^2$ is N.
In one variation of Formula I, Y$^2$ is H and X$^3$ is CH$_2$.
In one variation of Formula I, Y$^2$ is H, X$^3$ is CH$_2$, Z$^1$ is N and Z$^2$ is N.
In one variation of Formula I, X$^2$ is NS(=O)$_2$CH$_2$CH$_3$.
In one variation of Formula I, X$^2$ is NS(=O)$_2$CH$_2$CH$_3$, Y$^2$ is H, X$^3$ is CH$_2$, Z$^1$ is N and Z$^2$ is N.
In one variation of Formula I, Y$^1$ is methyl.
In one variation of Formula I, Y$^1$ is methyl, X$^2$ is NS(=O)$_2$CH$_2$CH$_3$, Y$^2$ is H, X$^3$ is CH$_2$, Z$^1$ is N and Z$^2$ is N.
In one variation of Formula I, Y$^1$ is H and X$^2$ is CH$_2$.
In one variation of Formula I, Y$^1$ is H, X$^2$ is CH$_2$, Y$^2$ is H, X$^3$ is CH$_2$, Z$^1$ is N and Z$^2$ is N.
In one variation of Formula I, Y$^3$ is methyl.
In one variation of Formula I, Y$^3$ is methyl, Y$^1$ is H, X$^2$ is CH$_2$, Y$^2$ is H, X$^3$ is CH$_2$, Z$^1$ is N and Z$^2$ is N.

The application provides the compound of Formula I selected from the group consisting of:
8-(1,1-Dioxo-1λ$^6$-thiomorpholin-4-yl)-3H-3,4,8a-triaza-as-indacene;
8-Cyclohexyl-3H-3,4,8a-triaza-as-indacene;
8-(2-Methyl-piperidin-1-yl)-3H-3,4,8a-triaza-as-indacene;
8-((3S,4S)-1-Ethanesulfonyl-4-methyl-piperidin-3-yl)-3H-3,4,8a-triaza-as-indacene;
8-((3S,4R)-1-Ethanesulfonyl-4-methyl-piperidin-3-yl)-3H-3,4,8a-triaza-as-indacene;
1-((1R,2S)-2-Methyl-cyclohexyl)-6H-2,3,5,6,8b-pentaaza-as-indacene;
1-((3R,4R)-1-Ethanesulfonyl-4-methyl-piperidin-3-yl)-6H-2,3,5,6,8b-pentaaza-as-indacene;
1-Cyclohexyl-6H-2,3,5,6,8b-pentaaza-as-indacene;
3-[(3S,4S)-4-Methyl-3-(6H-2,3,5,6,8b-pentaaza-as-indacen-1-yl)-piperidin-1-yl]-3-oxo-propionitrile;
1-Cyclohexyl-6H-2,5,6,8b-tetraaza-as-indacene;

The application provides a compound of Formula II

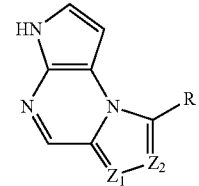

wherein:
Z$^1$ is CH or N;
Z$^2$ is CH or N;
R is lower alkyl, lower alkoxy, amino, cycloalkyl or heterocycloalkyl, optionally substituted with one more R$^1$; and
R$^1$ is lower alkyl, halogen, lower haloalkyl, lower alkoxy, lower alkylsulfonyl, or C(=O)R$^2$;
R$^2$ is H, amino, or R$^3$;
R$^3$ is lower alkyl, optionally substituted with one or more R$^4$; and
R$^4$ is halogen, lower alkoxy, cyano, or amino;
or a pharmaceutically acceptable salt thereof In one variation of Formula II, R is lower alkyl.
In one variation of Formula II, R is lower alkoxy.
In one variation of Formula II, R is amino.
In one variation of Formula II, R is cycloalkyl.
In one variation of Formula II, R is heterocycloalkyl.
In one variation of Formula II, R is heterocycloalkyl, R$^1$ is C(=O)R$^2$, R$^2$ is R$^3$, R$^3$ is lower alkyl, and R$^4$ is cyano.

In one aspect, the application provides a method for treating asthma comprising administering to a patient in need thereof a therapeutically effective amount of the compound of Formula I or Formula II.

In one aspect, the application provides a method for treating arthritis comprising administering to a patient in need thereof a therapeutically effective amount of the compound of Formula I or Formula II.

In one aspect, the application provides a method for treating rheumatoid arthritis comprising administering to a patient in need thereof a therapeutically effective amount of the compound of Formula I or Formula II.

In one aspect, the application provides a method for treating an inflammatory and/or autoimmune condition comprising administering to a patient in need thereof a therapeutically effective amount of the compound of Formula I or Formula II.

In one variation of the above method, the above method further comprises administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

In one aspect, the application provides a method for treating an inflammatory condition comprising administering to a patient in need thereof a therapeutically effective amount of the compound of Formula I or Formula II.

In one aspect, the application provides a method for inhibiting T-cell proliferative disorder comprising administering to a patient in need thereof a therapeutically effective amount of the compound of Formula I or Formula II.

In one aspect, the application provides a method for inhibiting T-cell proliferative disorder comprising administering to a patient in need thereof a therapeutically effective amount of the compound of Formula I or Formula II.

In one variation of the above method, the proliferative disorder is cancer.

In one aspect, the application provides a method for treating a B-cell proliferative disorder comprising administering to a patient in need thereof a therapeutically effective amount of the compound of Formula I or Formula II.

In one aspect, the application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I or Formula II.

In one aspect, the application provides a method for preventing or treating all forms of organ rejection, including acute allograft or xenograft rejection and chronic allograft or xenograft rejection, of vascularized or non-vascularized transplants, comprising administering to a patient in need thereof a therapeutically effective amount of the compound of Formula I or Formula II.

In one aspect, the application provides a method for inhibiting JAK3 activity comprising administering the compound of Formula I or Formula II, wherein the compound exhibits an $IC_{50}$ of 50 micromolar or less in an in vitro biochemical assay of JAK3 activity.

In one variation of the above method, the compound exhibits an $IC_{50}$ of 100 nanomolar or less in an in vitro biochemical assay of JAK3 activity.

In one variation of the above method, the compound exhibits an $IC_{50}$ of 10 nanomolar or less in an in vitro biochemical assay of JAK3 activity.

In one aspect, the application provides a method for treating an inflammatory condition comprising co-administering to a patient in need thereof an anti-inflammatory compound in combination with a therapeutically effective amount of the compound of Formula I or Formula II.

In one aspect, the application provides a method for treating an immune disorder comprising co-administering to a patient in need thereof an immunosuppressant compound in combination with a therapeutically effective amount of the compound of Formula I or Formula II.

The application provides a pharmaceutical composition comprising the compound of Formula I or Formula II, admixed with at least one pharmaceutically acceptable carrier, excipient or diluent.

In one variation, the above pharmaceutical composition further comprises an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

In one aspect, the application provides a use of the compound of Formula I or Formula II in the manufacture of a medicament for the treatment of an inflammatory disorder.

In one aspect, the application provides a use of the compound of Formula I or Formula II in the manufacture of a medicament for the treatment of an autoimmune disorder.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., R, R', or Q) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "-----" drawn through a bond each refer to the point of attachment of a functional group or other chemical moiety to the rest of the molecule of which it is a part. Thus, for example:

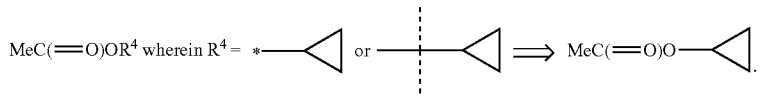

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "come together to form a bicyclic ring system" as used herein means join to form a bicyclic ring system, wherein each ring may be made up of either 4-7 carbon atoms or 4-7 carbon and heteroatoms, and may be saturated or unsaturated.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The definitions described herein may be appended to form chemically-relevant combinations, such as "heteroalkylaryl," "haloalkylheteroaryl," "arylalkylheterocyclyl," "alkylcarbonyl," "alkoxyalkyl," "cycloalkylalkyl" and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

Compounds of Formula I may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl", "aryl alkyl", or "aralkyl" are interpreted similarly except R' is an aryl radical. The terms "heteroaryl alkyl" or "heteroarylalkyl" are interpreted similarly except R' is optionally an aryl or a heteroaryl radical.

The term "haloalkyl" as used herein denotes a unbranched or branched chain alkyl group as defined above wherein 1, 2, 3 or more hydrogen atoms are substituted by a halogen. The term "lower haloalkyl" denotes a straight or branched chain hydrocarbon residue containing 1 to 6 carbon atoms, wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "hydroxyalkyl" as used herein denotes an alkyl radical as herein defined wherein one to three hydrogen atoms on different carbon atoms is/are replaced by hydroxyl groups.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "halogen" or "halo" as used herein means fluorine, chlorine, bromine, or iodine.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heterocycloalkyl", "heterocyclyl" or "heterocycle" as used herein denotes a monovalent saturated cyclic radical, consisting of one or more rings, preferably one to two rings, of three to eight atoms per ring, incorporating one or more ring carbon atoms and one or more ring heteroatoms (chosen from N, O or S(=O)$_{0-2}$), wherein the point of attachment can be through either a carbon atom or a heteroatom, and which can optionally be independently substituted with one or more, preferably one or two or three substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The phrase "organ rejection" includes acute allograft or xenograft rejection and chronic allograft or xenograft rejection in the setting of vascularized and/or non-vascularized (e.g. bone marrow, pancreatic islet cells) transplants.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), trimethylsilanyl-ethoxymethyl (SEM), tert-butyldimethylsilyl or t-BuMe$_2$Si (TBDMS), triethylamine (TEA or Et$_3$N), 2,2,6,6-tetramethylpiperidine 1-oxyl (TEMPO), triflate or CF$_3$SO$_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts exemplified compounds according to Formula I.

TABLE I

| COMPOUND | SYSTEMATIC NAME | STRUCTURE |
|---|---|---|
| I-1 | 8-(1,1-Dioxo-1$\lambda^6$-thiomorpholin-4-yl)-3H-3,4,8a-triaza-as-indacene | 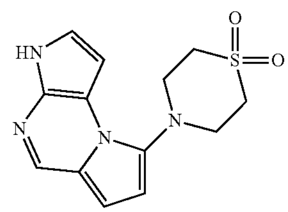 [SMILES: O=S1(=O)CCN(c2ccc3cnc4[nH]ccc4n23)CC1] |
| I-2 | 8-Cyclohexyl-3H-3,4,8a-triaza-as-indacene | 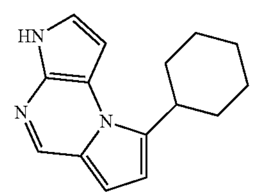 [SMILES: c1cc2c(ncc3ccc(C4CCCCC4)n32)[nH]1] |
| I-3 | 8-(2-Methyl-piperidin-1-yl)-3H-3,4,8a-triaza-as-indacene | 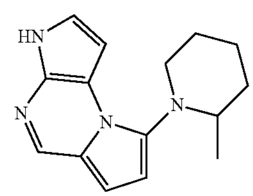 [SMILES: CC1CCCCN1c1ccc2cnc3[nH]ccc3n12] |
| I-4 | 8-((3S,4S)-1-Ethanesulfonyl-4-methyl-piperidin-3-yl)-3H-3,4,8a-triaza-as-indacene | 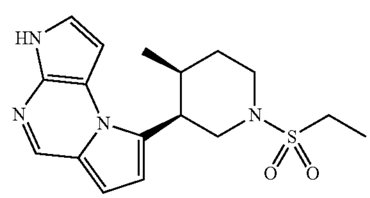 [SMILES: CCS(=O)(=O)N1CC[C@H](C)[C@H](c2ccc3cnc4[nH]ccc4n23)C1] |
| I-5 | 8-((3S,4S)-1-Ethanesulfonyl-4-methyl-piperidin-3-yl)-3H-3,4,8a-triaza-as-indacene | 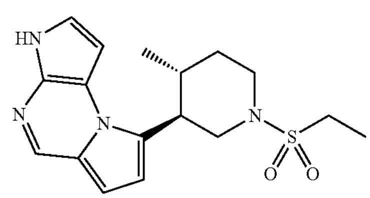 [SMILES: CCS(=O)(=O)N1CC[C@@H](C)[C@H](c2ccc3cnc4[nH]ccc4n23)C1] |
| I-6 | 1-((1R,2S)-2-Methyl-cyclohexyl)-6H-2,3,5,6,8b-pentaaza-as-indacene | 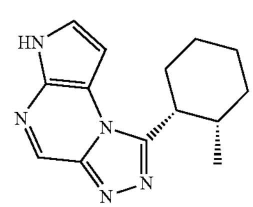 [SMILES: C[C@H]1CCCC[C@H]1c1nnc2cnc3[nH]ccc3n12] |

TABLE I-continued
| COMPOUND | SYSTEMATIC NAME | STRUCTURE |
|---|---|---|
| I-7 | 1-((3R,4R)-1-Ethanesulfonyl-4-methyl-piperidin-3-yl)-6H-2,3,5,6,8b-pentaaza-as-indacene | 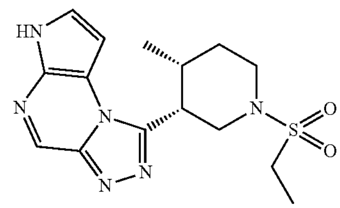 [SMILES: CCS(=O)(=O)N1CC[C@@H](C)[C@@H](c2nnc3cnc4[nH]ccc4n23)C1] |
| I-8 | 1-Cyclohexyl-6H-2,3,5,6,8b-pentaaza-as-indacene | 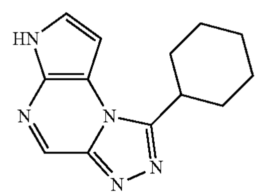 [SMILES: c1cc2c(ncc3nnc(C4CCCCC4)n32)[nH]1] |
| I-9 | 3-[(3S,4S)-4-Methyl-3-(6H-2,3,5,6,8b-pentaaza-as-indacen-1-yl)-piperidin-1-yl]-3-oxo-propionitrile | 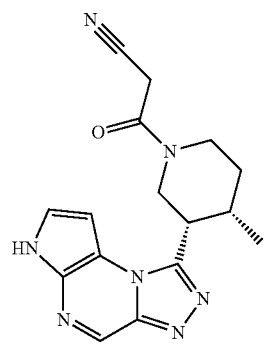 [SMILES: C[C@H]1CCN(C(=O)CC#N)C[C@H]1c1nnc2cnc3[nH]ccc3n12] |
| I-10 | 1-Cyclohexyl-6H-2,5,6,8b-tetraaza-as-indacene | 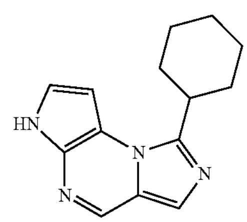 [SMILES: c1cc2c(ncc3cnc(C4CCCCC4)n32)[nH]1] |
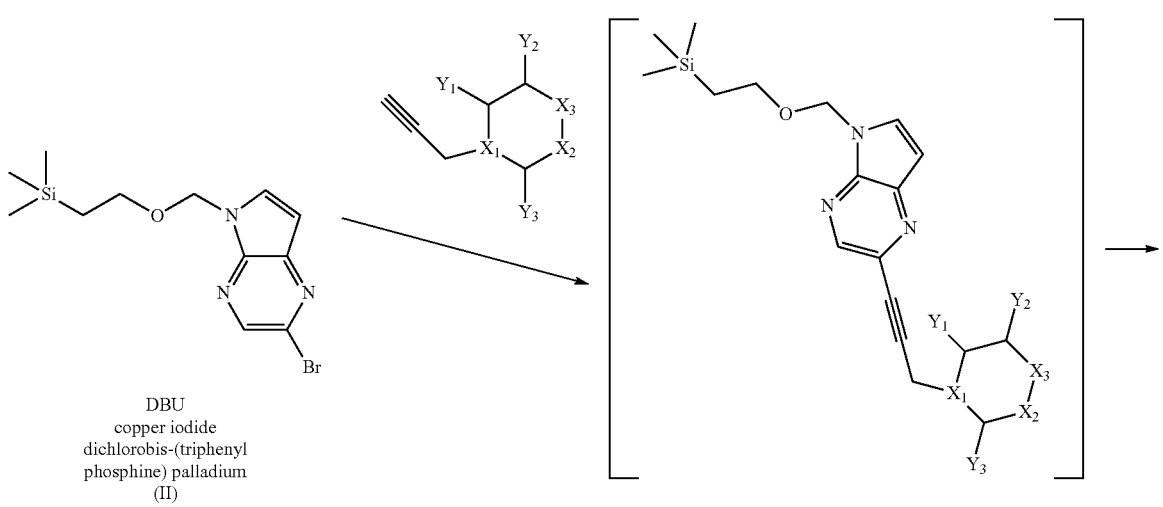
Scheme 1.

-continued

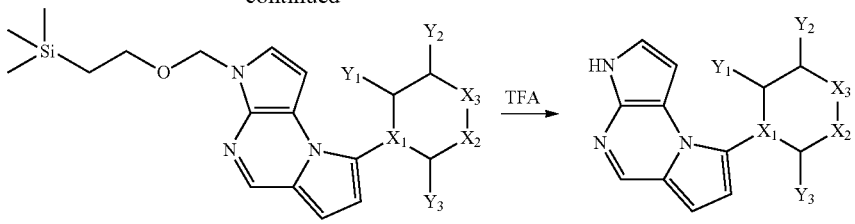

In the above Scheme 1, $X^1$ can be CH or N, $X^2$ can be $CH_2$, $NS(=O)_2R^1$, or $NC(=O)R^{1'}$, $R^1$ can be lower alkyl, $R^{1'}$ can be H, amino, or $R^{1''}$, $R^{1''}$ can be lower alkyl, optionally substituted with one or more $R^{1'''}$, $R^{1'''}$ can be halogen, lower alkoxy, cyano, or amino, $X^3$ can be $CHR^2$ or $S(=O)_2$, $R^2$ is H or lower alkyl, $Y^1$ can be H, lower alkyl, lower alkoxy, halogen, or lower haloalkyl, $Y^2$ can be H or lower alkyl, and $Y^3$ can be H, lower alkyl, lower alkoxy, halogen, or lower haloalkyl.

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof

EXAMPLES

Example 1

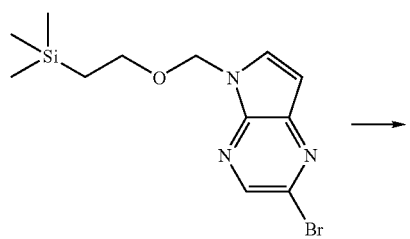

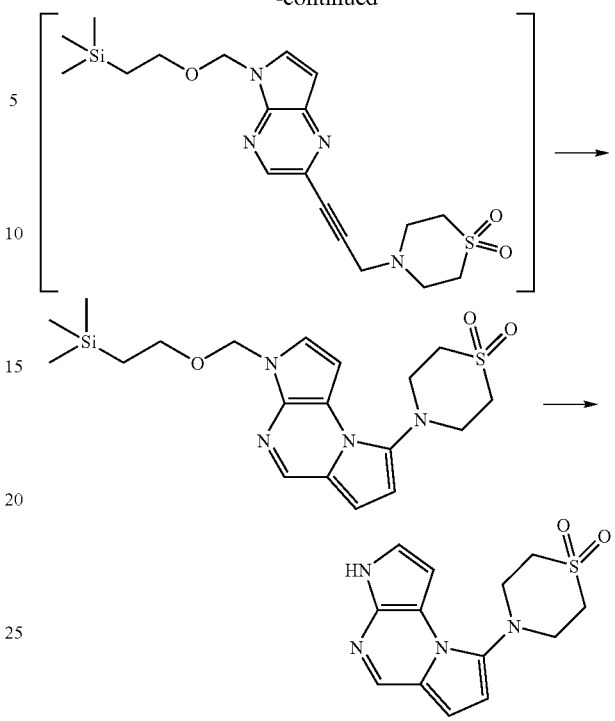

Preparation of 8-(1,1-Dioxo-1λ$^6$-thiomorpholin-4-yl)-3H-3,4,8a-triaza-as-indacene (2-Ethanesulfonyl-ethyl)-methyl-[3-(2-trimethylsilanyl-ethoxymethyl)-3H-3,4,8a-triaza-as-indacen-8-yl]-amine. A flask was charged with 2-bromo-5-(2-trimethylsilanyl-ethoxymethyl)-5H-pyrrolo[2,3-b]pyrazine (295 mg, 0.9 mmol), 4-propargyl-thiomorpholine-1,1-dioxide (commercial, 156 mg, 0.9 mmol), copper iodide (17 mg, 0.09 mmol), dichlorobis-(triphenylphosphine)palladium (II) (13 mg, 0.018 mmol) and DBU (0.4 mL, 2.7 mmol) in dry dimethyl acetamide (3 mL). The mixture was vacuum degassed and heated to 80° C. under argon. After 1.5 hours the material was warmed to 120° C. and stirred for 12 hours. The mixture was cooled to ambient and quenched via the addition of water (45 ml) and ethyl acetate (45 ml). The material was shaken in a reparatory funnel, and the ethyl acetate phase was collected. The aqueous phases were back extracted with ethyl acetate (2×40 ml), the organics combined, dried (MgSO$_4$), filtered and stripped. The remainder was purified by preparative TLC using 45% ethyl acetate in hexanes as eluant to provide 232 mg of (2-ethanesulfonyl-ethyl)-methyl-[3-(2-trimethylsilanyl-ethoxymethyl)-3H-3,4,8a-triaza-as-indacen-8-yl]-amine as a dark brown oil. MS (M+H)+=421.

8-(1,1-Dioxo-1λ$^6$-thiomorpholin-4-yl)-3H-3,4,8a-triaza-as-indacene. (2-Ethanesulfonyl-ethyl)-methyl-[3-(2-trimethylsilanyl-ethoxymethyl)-3H-3,4,8a-triaza-as-indacen-8-yl]-amine (68 mg, 0.16 mmol) was taken up in methylene chloride (3 mL) and TFA (2 mL) and lightly capped and stirred for 2 hours. The volatiles were removed on the rotovap and the remainder was taken up in CH$_2$Cl$_2$ (25 mL). The volatiles were stripped and the remainder placed on a drying pump for 30 minutes. The material was taken up methylene chloride (2 mL) and ethylene diamine (2 mL) and stirred for 1.5 hours. Ethyl acetate (40 ml) and brine (40 mL) was added and the material shaken in a separatory funnel. The ethyl acetate phase was collected and washed with an equal volume of brine solution. The aqueous phases were back extracted with ethyl acetate (2×30 ml), the organics combined, dried (MgSO4), filtered and stripped. The crude was purified via preparative TLC using 7% MeOH in CH$_2$Cl$_2$ as eluant to provide 49 mg of (2-ethanesulfonyl-ethyl)-methyl-(3H-3,4,8a-triaza-as-indacen-8-yl)-amine as a green-black crystalline solid. MS (M+H)+=291.

Example 2

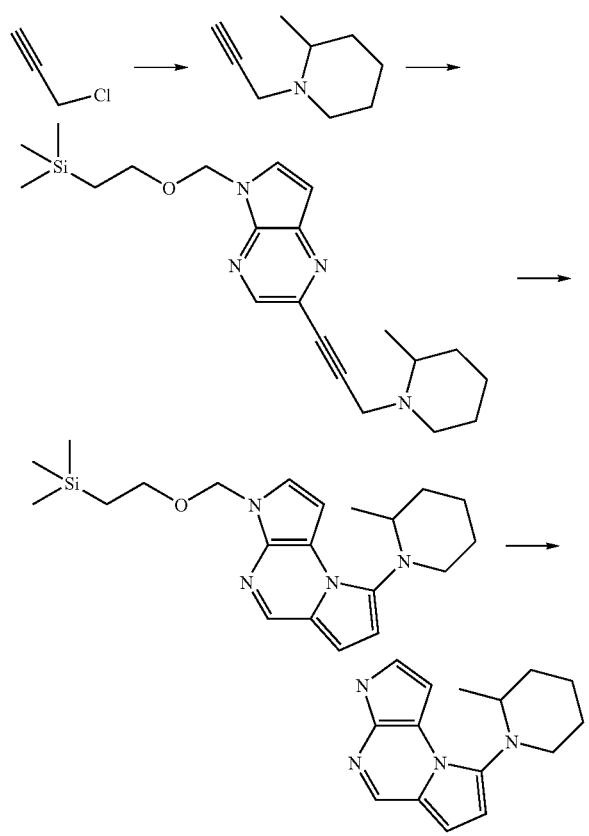

(+/−)-2-Methyl-1-prop-2-ynyl-piperidine. A flask was charged with propargyl chloride (17.27 g, 0.232 mol, 70 wt % in toluene) in dry methanol (21 mL) under nitrogen atmosphere. (+/−)-2-Methyl-piperidine (55 mL, 0.46 mol) in dry methanol (43 mL) was added via drop-wise addition over 30 minutes. The material was stirred overnight. The mixture was placed on a rotovap and about half the volume of methanol was stripped, providing a precipitate. The solid precipitate was removed by filtration, rinsing through with ether (150 mL). The filtrite was placed on the rotovap and concentrated. Another small amount of precipitate was removed by filtration. The remaining oily product was purified by distillation providing 7.23 g (bp=180-185° C.) of (+/−)-2-methyl-1-prop-2-ynyl-piperidine as a clear mobile oil.

(+/−)-2-[3-(2-Methyl-piperidin-1-yl)-prop-1-ynyl]-5-(2-trimethylsilanyl-ethoxymethyl)-5H-pyrrolo[2,3-b]pyrazine. A flask was charged with 2-bromo-5-(2-trimethylsilanyl-ethoxymethyl)-5H-pyrrolo[2,3-b]pyrazine (250 mg, 0.76 mmol), 2-propargyl-1-methyl-piperidine (105 mg, 0.76 mmol), copper iodide (15 mg, 0.076 mmol), dichlorobis-(triphenylphosphine)palladium (II) (11 mg, 0.02 mmol) and DBU (0.34 mL, 2.28 mmol) in dry dimethyl acetamide (3 mL). The mixture was vacuum degassed and heated to 120° C. and stirred for 10 hours. The mixture was cooled to ambient and quenched via the addition of water (45 ml) and ethyl acetate (45 ml). The material was shaken in a separatory funnel, and the ethyl acetate phase was collected. The aqueous phases were back extracted with ethyl acetate (2×40 ml), the organics combined, dried (MgSO4), filtered and stripped. The remainder was purified by preparative TLC using 15% ethyl acetate in hexanes as eluant. The plates were re-developed consecutively with 40% and then 60% ethyl acetate in hexanes. The product band was collected to provide 185 mg of (+/−)-2-[3-(2-methyl-piperidin-1-yl)-prop-1-ynyl]-5-(2-trimethylsilanyl-ethoxymethyl)-5H-pyrrolo[2,3-b]pyrazine as a golden yellow oil. MS (M+H)$^+$=385

(+/−)-8-(2-methyl-piperidin-1-yl)-3-(2-trimethylsilanyl-ethoxymethyl)-3H-3,4,8a-triaza-as-indacene. To a flask containing (+/−)-2-[3-(2-methyl-piperidin-1-yl)-prop-1-ynyl]-5-(2-trimethylsilanyl-ethoxymethyl)-5H-pyrrolo[2,3-b] pyrazine (185 mg, 0.48 mmol) was added copper iodide (37 mg, 0.19 mmol), and DBU (0.34 mL, 2.28 mmol) in dry dimethyl acetamide (1 mL). The mixture was vacuum degassed and heated to 130° C. and stirred for 3 hours. The mixture was cooled to ambient and quenched via the addition of water (30 ml) and ethyl acetate (30 ml). The material was shaken in a reparatory funnel, and the ethyl acetate phase was collected. The aqueous phases were back extracted with ethyl acetate (2×25 ml), the organics combined, dried (MgSO4), filtered and stripped. The remainder was purified by preparative TLC using 25% ethyl acetate in hexanes as eluant. The product band was collected to provide 36 mg of (+/−)-8-(2-methyl-piperidin-1-yl)-3-(2-trimethylsilanyl-ethoxymethyl)-3H-3,4,8a-triaza-as-indacene as a brown-black oil. Note that starting material (90 mg) was also recovered. This material was subjected to the identical reaction conditions as above (but over-night heating), to provide an extra 12 mg of product. MS (M+H)$^+$=385.

(+/−)-8-(2-Methyl-piperidin-1-yl)-3H-3,4,8a-triaza-as-indacene. (+/−)-8-(2-methyl-piperidin-1-yl)-3-(2-trimethylsilanyl-ethoxymethyl)-3H-3,4,8a-triaza-as-indacene (48 mg, 0.12 mmol) was SEM de-protected using the same procedure as described above in example 2, to provide a crude product. The material was purified by preparative TLC, eluting with 6% methanol in methylene chloride to provide semi-pure product. This material was re-subjected to preparative TLC, eluting with 8% methanol in methylene chloride to provide 15 mg of (+/−)-methyl-(1-methyl-pentyl)-(3H-3,4,8a-triaza-as-indacen-8-yl)-amine as a dark green solid. MS (M+H)$^+$=255.

Example 3

Preparation of
8-cyclohexyl-3H-3,4,8a-triaza-as-indacene

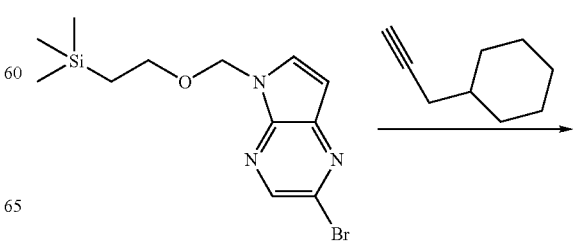

-continued

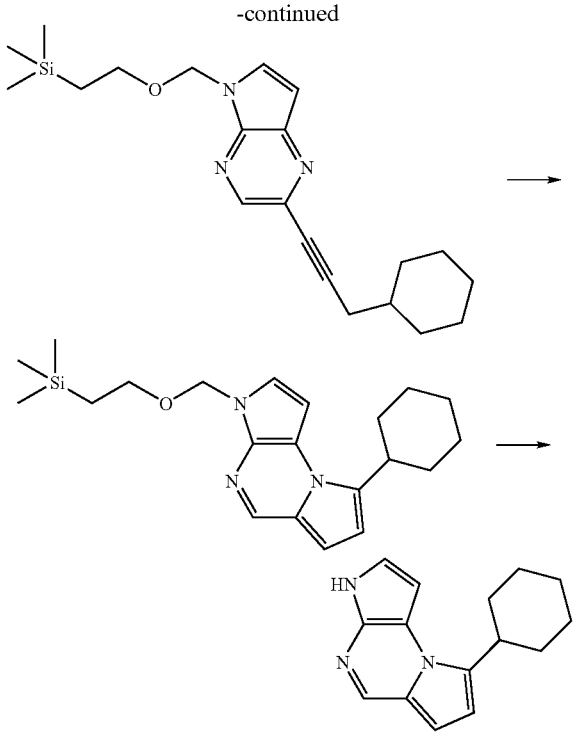

2-(3-Cyclohexyl-prop-1-ynyl)-5-(2-trimethylsilanyl-ethoxymethyl)-5H-pyrrolo[2,3-b]pyrazine. 2-Bromo-5-(2-trimethylsilanyl-ethoxymethyl)-5H-pyrrolo[2,3-b]pyrazine (402 mg, 1.22 mmol) and 3-cyclohexyl-1-propyne (745 mg, 6.1 mmol) were reacted under the same conditions as described in example 4 above. The crude product was adsorbed onto silica (1.5 g) and purified by silica gel chromatography, eluting with 5% to 20% ethyl acetate in hexanes to afford 395 mg of 2-(3-cyclohexyl-prop-1-ynyl)-5-(2-trimethylsilanyl-ethoxymethyl)-5H-pyrrolo[2,3-b]pyrazin as a light brown semi-mobile oil. MS (M+H)$^+$=370.

8-Cyclohexyl-3-(2-trimethylsilanyl-ethoxymethyl)-3H-3,4,8a-triaza-as-indacene. The 2-(3-cyclohexyl-prop-1-ynyl)-5-(2-trimethylsilanyl-ethoxymethyl)-5H-pyrrolo[2,3-b]pyrazin (395 mg, 1.07 mmol) was reacted under the same conditions as described in example 5 to provide a crude product. The material was purified by preparative TLC using 20% ethyl acetate in hexanes to afford 220 mg of 8-cyclohexyl-3-(2-trimethylsilanyl-ethoxymethyl)-3H-3,4,8a-triaza-as-indacene as a dark green-yellow semi-solid. MS (M+H)$^+$=370.

8-Cyclohexyl-3H-3,4,8a-triaza-as-indacene. 8-Cyclohexyl-3-(2-trimethylsilanyl-ethoxymethyl)-3H-3,4,8a-triaza-as-indacene (220 mg, 0.6 mmol) was SEM de-protected under the same conditions as described in example 2 to provide a crude product. This material was purified by preparative TLC, using 4.5% methanol in methylene chloride. The semi-pure product was crystallized from hot methylene chloride (containing a small amount of methanol) to provide 89 mg of 8-(1-methyl-hexyl)-3H-3,4,8a-triaza-as-indacene as a light green-grey solid. MS (M+H)$^+$=240.

Example 4

Preparation of trans-(+/−)-8-(1-ethanesulfonyl-4-methyl-piperidin-3-yl)-3H-3,4,8a-triaza-as-indacene

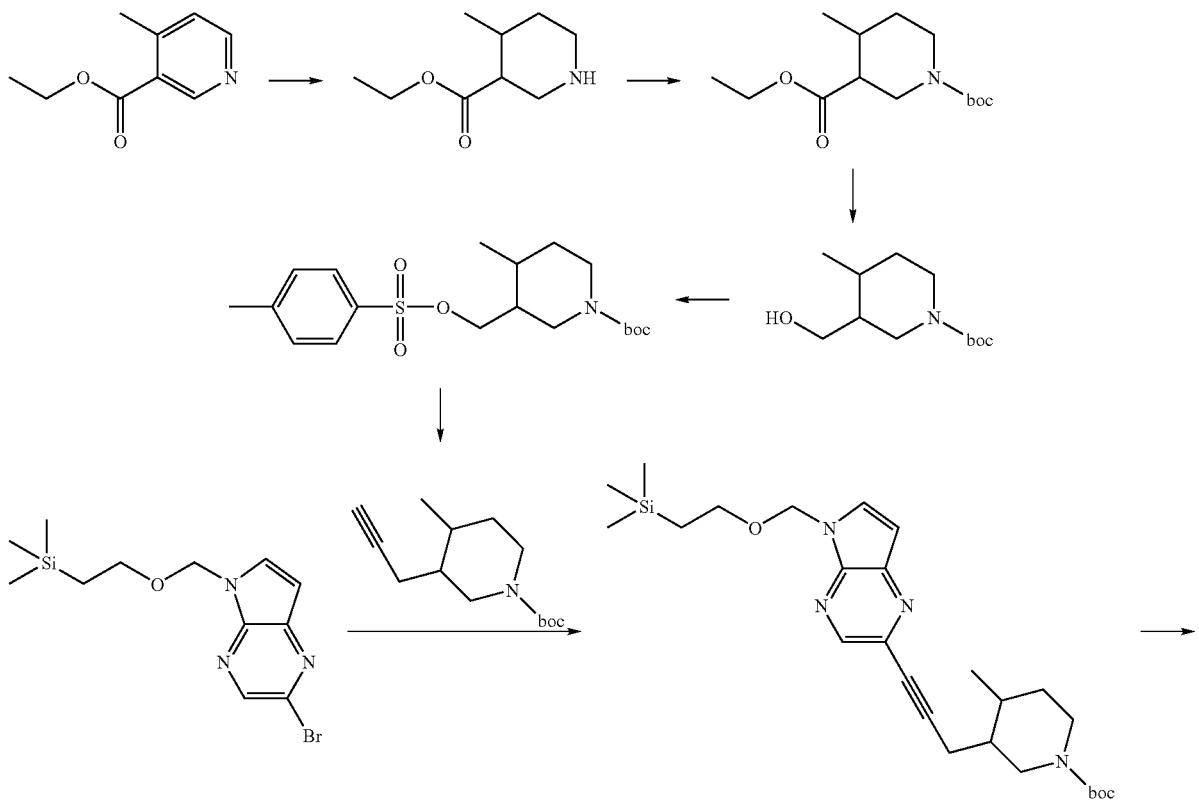

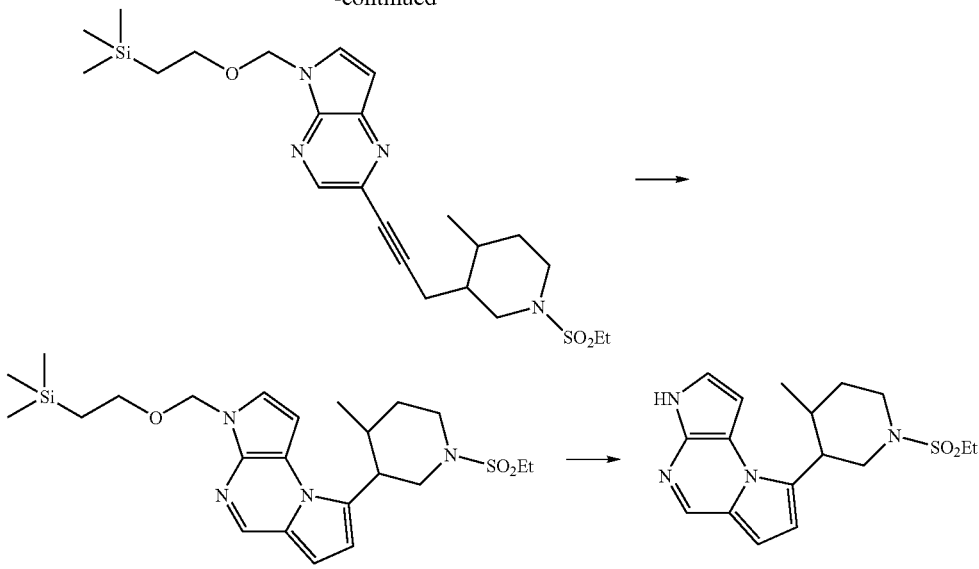

Ethyl-4-methylnicotinoate: To a flask containing 4-methylnicotinic acid 1.5 hydrochloride (9.6 g, 55.3 mmol), dissolved in dry absolute ethanol (120 mL) was added concentrated sulfuric acid (6 mL) via drop-wise addition. The material was heated to reflux temperature and stirred over night. The flask was cooled to ambient and about 85% of the solvent was removed on the rotovap. Ethyl acetate (40 mL) was added and the material was basified via drop-wise addition of an aqueous saturated sodium bicarbonate solution. Ethyl acetate (40 mL) and water (20 mL) was added and the material was shaken in a separatory funnel. The ethyl acetate phase was collected and washed with brine (60 mL). The aqueous phases were back extracted with ethyl acetate (2×50 mL), the organic phases were combined, dried (MgSO$_4$), filtered and stripped affording ethyl-4-methylnicotinoate as a brown mobile oil. MS (M+H)+=166.

(+/−)-4-Methyl-piperidine-3-carboxylic acid ethyl ester. A Parr bottle was charged with ethyl-4-methylnicotinoate (5.01 g, 30.32 mmol), L-(+)-tartaric acid (4.67 g, 31.2 mmoL) and platinum oxide (Adams catalyst, 827 mg). The material was taken up in absolute ethanol (100 mL) and shaken on the PARR overnight under hydrogen atmosphere (50 psi). The material was filtered through a plug of celite, and the filtrate was concentrated on the rotovap such that about 85% of the solvent was removed. The remainder was taken up in ethyl acetate (120 mL) and aqueous saturated sodium bicarbonate solution (120 mL) and shaken in a separatory funnel. The ethyl acetate phase was collected. The aqueous phase was treated with 2N sodium hydroxide solution (25 mL) and shaken with ethyl acetate (100 mL). The ethyl acetate phase was collected and the aqueous phase back extracted with ethyl acetate (100 mL). The organic phases were combined, dried (MgSO4), filtered and stripped to provide 4.7 g of (+/−)-4-methyl-piperidine-3-carboxylic acid ethyl ester as a mobile yellow oil. MS (M+H)+=172.

(+/−)-4-Methyl-piperidine-1,3-dicarboxylic acid 1-tert-butyl ester 3-ethyl ester. To a solution of (+/−)-4-methyl-piperidine-3-carboxylic acid ethyl ester (4.69 g, 27.4 mmol) and di-tert-butyldicarbonate (6.58 g, 30.1 mmol) in dry tetrahydrofuran (30 mL) was added 4-dimethylaminopyridine (135 mg, in 3 portions). The mixture was stirred under nitrogen atmosphere for 48 hours. The solvent was stripped on the rotovap and the crude was purified by silica gel chromatography, eluting with 1% to 20% ethyl acetate in hexanes to afford 7.08 g of (+/−)-4-methyl-piperidine-1,3-dicarboxylic acid 1-tert-butyl ester 3-ethyl ester as a clear semi-mobile oil. MS (M+Na)+=294.

(+/−)-3-Hydroxymethyl-4-methyl-piperidine-1-carboxylic acid tert-butyl ester. A flask containing (+/−)-4-methyl-piperidine-1,3-dicarboxylic acid 1-tert-butyl ester 3-ethyl ester (5.96 g, 21.94 mmol) in dry tetrahydrofuran (40 mL) was cooled to 0° C. (ice bath) under argon atmosphere. A solution of lithium aluminum hydride (19.4 mL, 1M in tetrahydrofuran) was added via slow drop-wise addition. The cooled mixture was stirred for 2 hours. A solution of 1 M hydrochloric acid (23 mL) was added via slow drop-wise addition. After 10 minutes powdered magnesium sulfate was added followed by the addition of ethyl acetate (80 mL). The mixture was filtered through a plug of celite, rinsing well with ethyl acetate. The filtrate was stripped providing 5.08 g of (+/−)-3-hydroxymethyl-4-methyl-piperidine-1-carboxylic acid tert-butyl ester as a clear semi-mobile oil. MS (M+Na)$^+$=252.

(+/−)-4-Methyl-3-(toluene-4-sulfonyloxymethyl)-piperidine-1-carboxylic acid tert-butyl ester. A flask was charged with (+/−)-4-methyl-3-methanol-N-tert-butoxycarbonyl-piperidine (5.08 g, assume 21.5 mmol), taken up in dry pyridine (30 mL) and cooled to 0° C. (ice bath) under nitrogen atmosphere. To the cooled mixture was added 4-toluenesulfonyl chloride 4.51 g, 23.65 mmol) in two portions over 5 minutes. The mixture was stirred and warmed to ambient overnight. The mixture was again cooled to 0° C. and additional 4-toluenesulfonyl chloride (1.2 g) was added. The mixture was stirred and warmed to ambient over 24 hours. The pyridine was stripped on the rotovap. The remainder was taken up in ethyl acetate (80 mL) and water (80 mL) and shaken in a separatory funnel. The ethyl acetate phase was collected and washed with an equal volume of brine. The aqueous phases were back extracted with ethyl acetate (2×60 mL). The organics were combined, dried (MgSO$_4$), filtered and stripped. The crude was taken up in methylene chloride and adsorbed onto 25 g of powdered silica gel. The material was purified by silica gel chromatography, eluting with 3% to 25% ethyl acetate in hexanes, providing 6.91 g of (+/−)-4-methyl-3-

(toluene-4-sulfonyloxymethyl)-piperidine-1-carboxylic acid tert-butyl ester as a clear semi-mobile oil. MS (M+Na)$^+$=406.

(+/−)-4-Methyl-3-prop-2-ynyl-piperidine-1-carboxylic acid tert-butyl ester. A flask containing lithium acetylide, ethylene diamine complex (3.82 g, 37.4 mmol) was taken up in dry DMSO (50 mL) and cooled to approximately 8° C. (dilute ice bath) under argon atmosphere. To the cooled mixture was added a solution of (+/−)-4-methyl-3-(toluene-4-sulfonyloxymethyl)-piperidine-1-carboxylic acid tert-butyl ester (6.91 g, 17.79 mmol) in dry DMSO (40 mL), via slow drop-wise addition. The dark brown-black mixture was stirred vigorously to ambient temperature for 4.5 hours. The reaction was carefully quenched via the addition of a saturated solution of aqueous ammonium chloride (60 mL), followed by the addition of diethyl ether (120 mL) and water (50 mL). The mixture was transferred to a separatory funnel and shaken. The ether phase was collected and shaken with an equal volume of brine. The aqueous phases were back extracted with diethyl ether (2×100 mL). The crude was taken up in methylene chloride (40 mL) and adsorbed onto 25 g of silica gel. The solvent was stripped and the crude material was purified by silica gel chromatography, eluting with 4% to 20% ethyl acetate in hexanes, providing 2.21 g of (+/−)-4-methyl-3-prop-2-ynyl-piperidine-1-carboxylic acid tert-butyl ester as a clear mobile oil. MS (M+Na)$^+$=260.

(+/−)-4-Methyl-3-{3-[5-(2-trimethylsilanyl-ethoxymethyl)-5H-pyrrolo[2,3-b]pyrazin-2-yl]-prop-2-ynyl}-piperidine-1-carboxylic acid tert-butyl ester. 2-Bromo-5-(2-trimethylsilanyl-ethoxymethyl)-5H-pyrrolo[2,3-b]pyrazine (1.67 g, 5.09 mmol) and (+/−)-4-methyl-3-prop-2-ynyl-piperidine-1-carboxylic acid tert-butyl ester (1.21 g, 5.09 mmol) were reacted under the same conditions as described in example 4 above. The crude product was adsorbed onto silica (10 g) and purified by silica gel chromatography, eluting with 5% to 30% ethyl acetate in hexanes to afford 2.11 g of (+/−)-4-methyl-3-{3-[5-(2-trimethylsilanyl-ethoxymethyl)-5H-pyrrolo[2,3-b]pyrazin-2-yl]-prop-2-ynyl}-piperidine-1-carboxylic acid tert-butyl ester as a yellow viscous oil. MS (M+H)$^+$=485.

(+/−)-2-[3-(1-Ethanesulfonyl-4-methyl-piperidin-3-yl)-prop-1-ynyl]-5-(2-trimethylsilanyl-ethoxymethyl)-5H-pyrrolo[2,3-b]pyrazine. To a flask containing a solution of (+/−)-4-methyl-3-{3-[5-(2-trimethylsilanyl-ethoxymethyl)-5H-pyrrolo[2,3-b]pyrazin-2-yl]-prop-2-ynyl}-piperidine-1-carboxylic acid tert-butyl ester (505 mg, 1.04 mmol) in methylene chloride (4 mL) was added a 25% solution of anhydrous HCl in dioxane (3 mL). The mixture was lightly capped and stirred for 45 minutes. The solvent was stripped on the rotovap and the remainder was taken up in methylene chloride (15 mL) and stripped. This was repeated one more time to provide a yellow foamy solid. The crude material was taken up in dry methylene chloride and cooled to 0° C. (ice bath) under argon atmosphere. Ethyl diisopropyl amine was added and the material was stirred for 5 minutes. Ethane sulfonyl chloride (0.1 mL, 1.1 mmol) was slowly added via syringe and the material was stirred for 10 minutes. The cooling bath was removed and stirring continued for 1.5 hours. The crude mixture was taken up in water (40 mL) and methylene chloride (40 mL) and shaken in a reparatory funnel. The organic phase was collected and the aqueous phases were back extracted with methylene chloride (2×30 ml), the organics combined, dried (MgSO4), filtered and stripped. The remainder was purified by preparative TLC eluting with 50% ethyl acetate in hexanes. The product band was collected providing 395 mg of (+/−)-2-[3-(1-ethanesulfonyl-4-methyl-piperidin-3-yl)-prop-1-ynyl]-5-(2-trimethylsilanyl-ethoxymethyl)-5H-pyrrolo[2,3-b]pyrazine as a viscous yellow oil. MS (M+H)$^+$=477.

(+/−)-8-(1-Ethanesulfonyl-4-methyl-piperidin-3-yl)-3-(2-trimethylsilanyl-ethoxymethyl)-3H-3,4,8a-triaza-as-indacene. To a flask containing (+/−)-2-[3-(1-ethanesulfonyl-4-methyl-piperidin-3-yl)-prop-1-ynyl]-5-(2-trimethylsilanyl-ethoxymethyl)-5H-pyrrolo[2,3-b]pyrazine (395 mg, 0.83 mmol) was added copper iodide (79 mg, 0.41 mmol), and DBU (0.57 mL, 3.8 mmol) in dry dimethyl acetamide (4 mL). The mixture was vacuum degassed and the flask was wrapped with tin foil (protect from light) and heated to 130° C. and stirred for 5 hours. Additional copper iodide (110 mg) was added and the mixture was stirred for another 6 hours and then cooled to ambient with over-night stirring. The material was taken up in water (30 mL) and ethyl acetate (30 mL), transferred to a reparatory funnel and shaken. The organic phase was collected and shaken with an equal volume of brine. The aqueous phases were back extracted with ethyl acetate (2×25 ml), the organics combined, dried (MgSO$_4$), filtered and stripped. The remainder was purified by preparative TLC eluting with 45% ethyl acetate in hexanes (develop plates in the dark). A less polar component was collected providing 23 mg of semi-pure trans-(+/−)-8-(1-ethanesulfonyl-4-methyl-piperidin-3-yl)-3-(2-trimethylsilanyl-ethoxymethyl)-3H-3,4,8a-triaza-as-indacene product. MS (M+H)$^+$=477. Also 17 mg of a more polar cis-(+/−)-8-(1-ethanesulfonyl-4-methyl-piperidin-3-yl)-3-(2-trimethylsilanyl-ethoxymethyl)-3H-3,4,8a-triaza-as-indacene product was collected. MS (M+H)$^+$=477.

Trans-(+/−)-8-(1-ethanesulfonyl-4-methyl-piperidin-3-yl)-3H-3,4,8a-triaza-as-indacene. Trans-(+/−)-8-(1-ethanesulfonyl-4-methyl-piperidin-3-yl)-3-(2-trimethylsilanyl-ethoxymethyl)-3H-3,4,8a-triaza-as-indacene (23 mg, 0.05 mmol) was SEM de-protected under the same conditions as described in example 2 (but protect from light) to provide a crude product. This material was purified by preparative TLC (in the dark), using 5% methanol in methylene chloride. The product band was collected to afford 5 mg of trans-(+/−)-8-(1-ethanesulfonyl-4-methyl-piperidin-3-yl)-3H-3,4,8a-triaza-as-indacene as a light green-brown solid. MS (M+H)$^-$=347.

Example 5

Preparation of cis-(+/−)-8-(1-ethanesulfonyl-4-methyl-piperidin-3-yl)-3H-3,4,8a-triaza-as-indacene Cis-(+/−)-8-(1-ethanesulfonyl-4-methyl-piperidin-3-yl)-3H-3,4,8a-triaza-as-indacene. Cis-(+/−)-8-(1-ethanesulfonyl-4-methyl-piperidin-3-yl)-3-(2-trimethylsilanyl-ethoxymethyl)-3H-3,4,8a-triaza-as-indacene (17 mg, 0.04 mmol) was SEM de-protected under the same conditions as described in example 2 (but protect from light) to provide a crude product. This material was purified by preparative TLC (in the dark), using 5% methanol in methylene chloride. The product band was collected to afford 6 mg of cis-(+/−)-8-(1-ethanesulfonyl-4-methyl-piperidin-3-yl)-3H-3,4,8a-triaza-as-indacene as a green-brown solid. MS (M+H)$^+$=347.

Example 6

Preparation of (+/−)-1-(2-methyl-cyclohexyl)-6H-2,3,5,6,8b-pentaaza-as-indacene

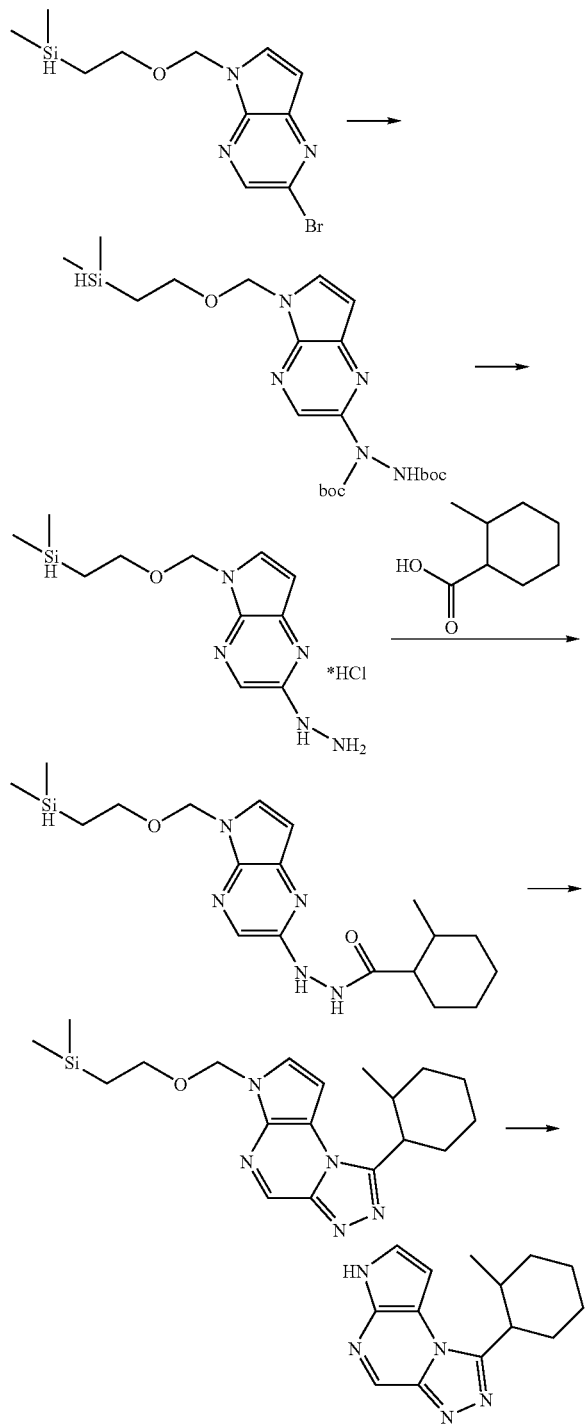

N'-[5-(2-Trimethylsilanyl-ethoxymethyl)-5H-pyrrolo[2,3-b]pyrazin-2-yl]-hydrazine-1,2-bis-(carboxylic acid tert-butyl ester). A flask was charged with di-tert-butyl-hydrazodiformate (924 mg, 3.97 mmol), tris(dibenzylideneacetone)dipalladium(0) (182 mg, 0.2 mmol), 1,1'-bis(diphenylphosphino)ferrocene (330 mg, 0.6 mmol) and cesium carbonate (1.62 g, 4.96 mmol) under argon atmosphere. To this mixture was added a solution of 2-bromo-5-(2-dimethylsilanyl-ethoxymethyl)-5H-pyrrolo[2,3-b]pyrazine (1.5 g, 4.57 mmol) in dry toluene (30 mL). The mixture was vacuum de-gassed under argon and heated to 100° C. for 4 hours. Additional tris(dibenzylideneacetone)dipalladium(0) (55 mg) and 1,1'-bis(diphenylphosphino)ferrocene (99 mg) were added and heating continued for 10 hours. The material was cooled to ambient. Water (80 mL) and methylene choride (80 mL) were added and the mixture was shaken in a separatory funnel. The organic phase was collected and the aqueous phase was back-extracted with methylene chloride (2×60 mL). The methylene chloride phases were combined, dried (MgSO$_4$), filtered and stripped. The crude remainder was purified by silica gel chromatography using a gradient of 5 to 45% ethyl acetate in hexanes to afford 1.37 g of N'-[5-(2-trimethylsilanyl-ethoxymethyl)-5H-pyrrolo[2,3-b]pyrazin-2-yl]-hydrazine-1,2-bis-(carboxylic acid tert-butyl ester). as a white-yellow solid. MS (M+Na)+=502

[5-(2-Trimethylsilanyl-ethoxymethyl)-5H-pyrrolo[2,3-b]pyrazin-2-yl]-hydrazine hydrochloride. To a solution of N'-[5-(2-trimethylsilanyl-ethoxymethyl)-5H-pyrrolo[2,3-b]pyrazin-2-yl]-hydrazine-1,2-bis-(carboxylic acid tert-butyl ester). (854 mg, 1.78 mmol) in dichloromethane (2 mL) was added a solution of dry 12% hydrochloric acid in ethyl acetate (4 mL). The material was lightly capped and stirred for 3.5 hours. The solvent was stripped and the remainder was placed on high vacuum/rotovap for about 2 hours, providing 554 mg of [5-(2-trimethylsilanyl-ethoxymethyl)-5H-pyrrolo[2,3-b]pyrazin-2-yl]-hydrazine hydrochloride as a yellow solid product. MS (M+H)+=280.

(+/−)-2-Methyl-cyclohexanecarboxylic acid-N'-[5-(2-trimethylsilanyl-ethoxymethyl)-5H-pyrrolo[2,3-b]pyrazin-2-yl]-hydrazide. A flask containing a mixture of [5-(2-trimethylsilanyl-ethoxymethyl)-5H-pyrrolo[2,3-b]pyrazin-2-yl]-hydrazine hydrochloride (336 mg, 1.06 mmol) and (+/−)-2-methyl-1-cyclohexane-carboxylic acid (0.18 mL, 1.22 mmol) in dry dichloromethane (11 mL) was cooled to 0° C. (ice bath) under nitrogen atmosphere. To this cooled mixture was added triethylamine (0.31 mL, 2.1 mmol) and EDCI (278 mg, 1.45 mmol). After 30 minutes the cooling bath was removed and the material was stirred for 3 hours. An aqueous solution of 5% sodium bicarbonate (40 mL) and methylene chloride (30 mL) were added and the mixture was shaken in a reparatory funnel. The organic phase was collected and washed with brine (40 mL). The aqueous phases were back extracted with methylene chloride (2×30 mL). The organic phases were combined, dried (MgSO$_4$), filtered and stripped. The crude remainder was purified by preparative TLC, using 45% ethyl acetate in hexanes to elute. The product band was collected, affording 152 mg of (+/−)-2-methyl-cyclohexanecarboxylic acid-N'-[5-(2-trimethylsilanyl-ethoxymethyl)-5H-pyrrolo[2,3-b]pyrazin-2-yl]-hydrazide as a golden brown oil, which solidified on standing. MS (M+H)+=404.

(+/−)-1-(2-Methyl-cyclohexyl)-6-(2-trimethylsilanyl-ethoxymethyl)-6H-2,3,5,6,8b-pentaaza-as-indacene. A solution of (+/−)-2-methyl-cyclohexanecarboxylic acid-N'-[5-(2-trimethylsilanyl-ethoxymethyl)-5H-pyrrolo[2,3-b]pyrazin-2-yl]-hydrazide (115 mg, 0.29 mmol) in tetrahydrofuran (3.7 mL) and carbon tetrachloride (2.8 mL) was cooled to 0° C. (ice bath) under argon atmosphere. N,N-Diisopropylethylamine (0.4 mL, 2.3 mmol) was added followed by the addition of triethylphosphine solution (0.87 mL, 1M in THF) via slow drop-wise addition over 2 minutes. The mixture was stirred to ambient temperature over night. Water (40 mL) and ethyl acetate (40 mL) were added and the mixture was stirred vigorously for 10 minutes. The organic phase was collected and the aqueous phase was back extracted with ethyl acetate (2×30 mL). The combined organic phases were combined, dried (MgSO4), filtered and stripped. The crude remainder was purified via preparative TLC, eluting with 33% ethyl acetate in hexanes. The plate was developed a second time with 50% ethyl acetate in hexanes. A less polar band was collected providing 32 mg of semi-pure product. A more polar fraction contained 23 mg of pure (+/−)-1-(2-methyl-cyclohexyl)-6H-2,3,5,6,8b-pentaaza-as-indacene as a yellow-brown semi-solid. MS (M+H)+=386.

(+/−)-1-(2-Methyl-cyclohexyl)-6H-2,3,5,6,8b-pentaaza-as-indacene. (+/−)-(2-Methyl-cyclohexyl)-6H-2,3,5,6,8b-pentaaza-as-indacene (23 mg, 0.06 mmol) was deprotected under the same conditions as described in example 2 to provide a crude product. This material was purified by preparative TLC, using 4% methanol in methylene chloride, and eluting a second time with 6% methanol in dichloromethane. Impure product was collected and re-purified by preparative TLC, eluting first with 80% ethyl acetate in hexanes and finally with 100% ethyl acetate as eluant. The product band was collected to provide 13 mg of (+/−)-1-(2-methyl-cyclohexyl)-6H-2,3,5,6,8b-pentaaza-as-indacene as a yellow-brown solid. MS (M+H)+=256.

Example 7

Preparation of (+/−)-1-(1-ethanesulfonyl-trans-4-methyl-piperidin-3-yl)-6H-2,3,5,6,8b-pentaaza-as-indacene

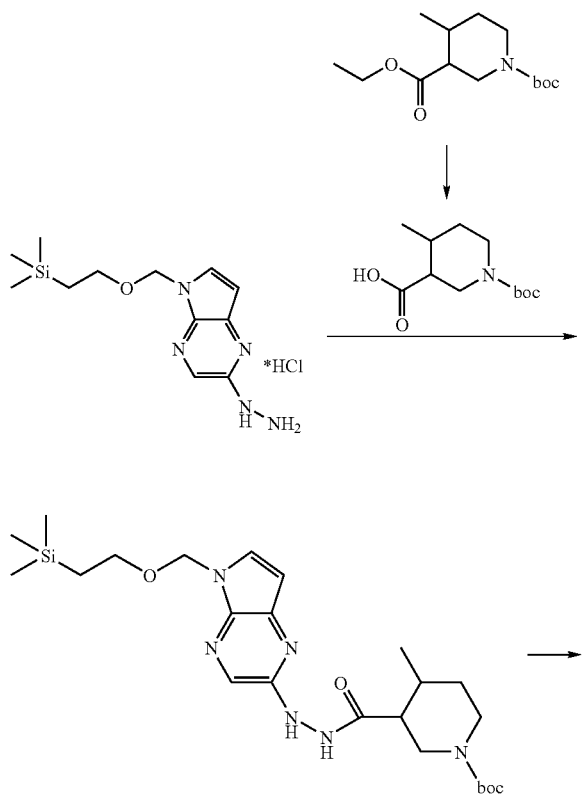

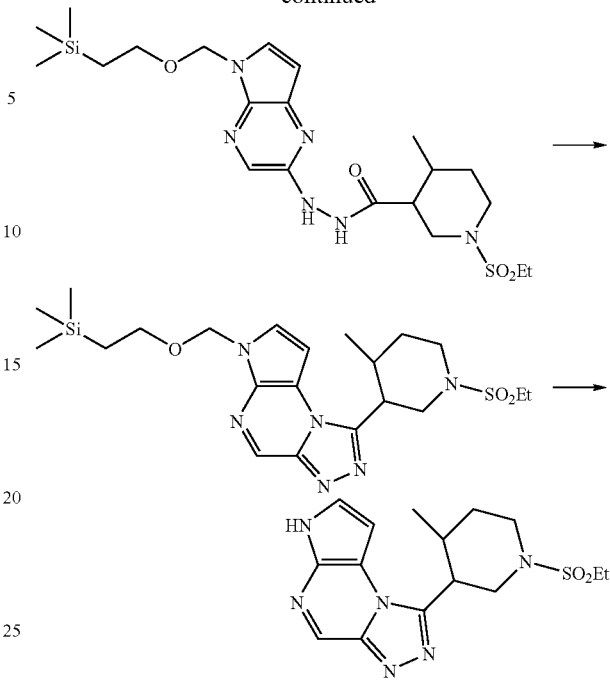

Trans-(+/−)-4-Methyl-piperidine-1,3-dicarboxylic acid 1-tert-butyl ester: To a flask containing (+/−)-4-methyl-piperidine-1,3-dicarboxylic acid 1-tert-butyl ester 3-ethyl ester (1.12 g, 4.1 mmol; from example 8 above) was taken up in tetrahydrofuran (12 mL) and methanol (3 mL) and cooled to 0° C. (ice bath). A solution of lithium hydroxide (4.5 mL, 1M) was added and the mixture was warmed to ambient over 3 hours. Extra methanol (2 mL) was added and the material was heated to 60° C. (oil bath) for 5.5 hours. The mixture was cooled to ambient and treated with 1N hydrochloric acid solution (4.7 mL) with vigorous stirring. The solvent was stripped and the remainder was dried under high vacuum for several hours, providing 1.06 g of mainly trans-(+/−)-4-methyl-piperidine-1,3-dicarboxylic acid 1-tert-butyl ester: as a off-white solid. MS (M−H)−=242.

(+/−)-3-{N'-[5-(2-Trimethylsilanyl-ethoxymethyl)-5H-pyrrolo[2,3-b]pyrazin-2-yl]-hydrazinocarbonyl}-trans-4-methyl-piperidine-1-carboxylic acid tert-butylester. A mixture of [5-(2-trimethylsilanyl-ethoxymethyl)-5H-pyrrolo[2,3-b]pyrazin-2-yl]-hydrazine hydrochloride (510 mg, 1.6 mmol, from example 15) and trans-(+/−)-4-methyl-piperidine-1,3-dicarboxylic acid 1-tert-butyl ester (480 mg, 1.9 mmol) were reacted under similar conditions to those described in example 16,to provide a crude product. Purification by preparative TLC, eluting with 55% ethyl acetate in hexanes afforded 200 mg of (+/−)-3-{N'-[5-(2-trimethylsilanyl-ethoxymethyl)-5H-pyrrolo[2,3-b]pyrazin-2-yl]-hydrazinocarbonyl}-trans-4-methyl-piperidine-1-carboxylic acid tert-butylester as a brown viscous oil. MS (M+H)+=505.

(+/−)-1-Ethanesulfonyl-trans-4-methyl-piperidine-3-carboxylic acid N'-[5-(2-trimethylsilanyl-ethoxymethyl)-5H-pyrrolo[2,3-b]pyrazin-2-yl]-hydrazide. (+/−)-3-{N'-[5-(2-trimethylsilanyl-ethoxymethyl)-5H-pyrrolo[2,3-b]pyrazin-2-yl]-hydrazinocarbonyl}-trans-4-methyl-piperidine-1-carboxylic acid tert-butylester (200 mg, 0.4 mmol) was reacted under similar conditions to those described in Example 17,above. The crude product was purified by preparative TLC, providing 107 mg of (+/−)-1-ethanesulfonyl-trans-4-methyl-piperidine-3-carboxylic acid N'-[5-(2-trimethylsilanyl-ethoxymethyl)-5H-pyrrolo[2,3-b]pyrazin-2-yl]-hydrazide as a yellow viscous oil. MS (M+H)+=497.

(+/−)-1-(1-Ethanesulfonyl-trans-4-methyl-piperidin-3-yl)-6-(2-trimethylsilanyl-ethoxymethyl)-6H-2,3,5,6,8b-pentaaza-as-indacene. (+/−)-Ethanesulfonyl-trans-4-methyl-piperidine-3-carboxylic acid N'-[5-(2-trimethylsilanyl-ethoxymethyl)-5H-pyrrolo[2,3-b]pyrazin-2-yl]-hydrazide (107 mg, 0.22 mmol) was cyclized to triazolo-tricyclic product using similar conditions to those described in example 17 above [however, after over-night stirring an extra 4 equivalents of N,N-diisopropylethylamine and an extra 3 equivalents of triethylphosphine were added and the mixture was stirred an extra 6 hours before work up]. The crude product was purified by preparative TLC, eluting with 90% ethyl acetate in hexanes. The impure product was collected and purified again by preparative TLC eluting first with 3.75% methanol in methylene chloride and then a second time with 5% methanol in methylene chloride. The product band was collected to afford 41 mg of (+/−)-1-(1-ethanesulfonyl-trans-4-methyl-piperidin-3-yl)-6-(2-trimethylsilanyl-ethoxymethyl)-6H-2,3,5,6,8b-pentaaza-as-indacene as a light yellow-white powder. MS (M+H)+=479.

(+/−)-1-(1-Ethanesulfonyl-trans-4-methyl-piperidin-3-yl)-6H-2,3,5,6,8b-pentaaza-as-indacene. (+/−)-1-(1-Ethanesulfonyl-trans-4-methyl-piperidin-3-yl)-6-(2-trimethylsilanyl-ethoxymethyl)-6H-2,3,5,6,8b-pentaaza-as-indacene (41 mg, 0.09 mmol) was SEM de-protected under similar conditions to those described in Example 2 above. The crude product was purified by preparative TLC, eluting first with 5% methanol in methylene chloride and then re-developing in 7% methanol in methylene chloride to provide 25 mg of (+/−)-1-(1-ethanesulfonyl-trans-4-methyl-piperidin-3-yl)-6H-2,3,5,6,8b-pentaaza-as-indacene as a light yellow-white powder. MS (M+H)+=349.

Example 8

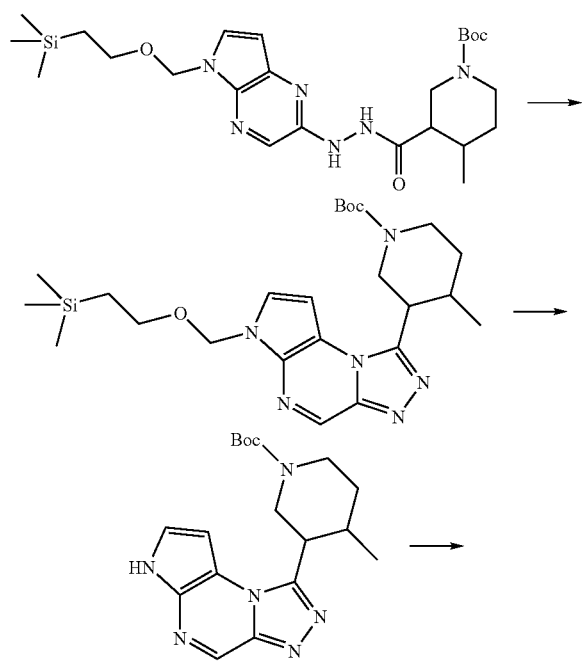

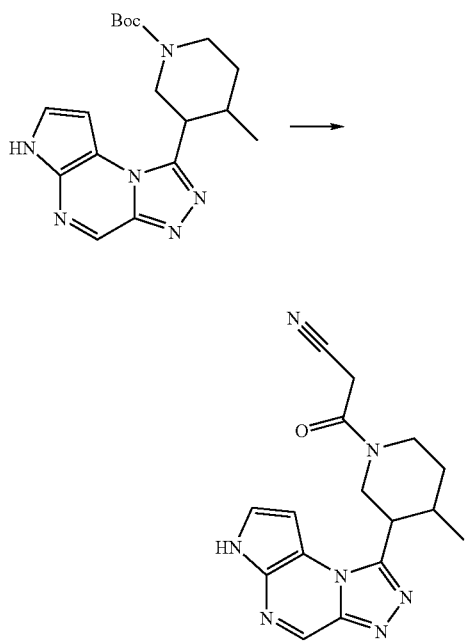

A solution SEM pyrrolopyrazine (269 mg, 0.534 mmol) in 7 mL of THF and 5.5 mL of carbon tetrachloride was cooled to 0° C. Diisopropylethyl amine (950 µL, 5.34 mmol) was added followed by slow addition of triethylphosphine (3.2 mL, 3.2 mmol, 1M in THF) over five minutes. After warming to room temperature, reaction mixture was stirred over 40 h. LCMS showed 92% conversion. Diisopropylethyl amine (316 µL, 1.78 mmol) was added followed by slow addition of triethylphosphine (1.06 mL, 1.06 mmol, 1 M in THF) at 0° C. Reaction mixture was poured into 60 mL of water and 60 mL of EtOAc and stirred for 20 min. The organic phase was collected and the aqueous phase was back extracted with ethyl acetate (2×30 mL). The combined organic phases were combined, dried (MgSO4), filtered and stripped. The crude residue was purified by SiO$_2$ chromatography eluting with a 25-70% ethyl acetate in hexanes gradient to afford 130 mg (50%) of compound X as a brown oil. MS (M+H)+=357.

A solution of the SEM protected pyrrolopyrazine (130 mg, 0.267 mmol) in THF (12 mL) was treated with TBAF (0.8 mL, 1M solution in THF) at rt. After stirring at rt for 24 h, TBAF (0.4 mL, 1M solution in THF) was added and the mixture was stirred at 60° C. for another 24 h. Water and ethyl acetate were added. The organic phase was collected and the aqueous phase was back extracted with ethyl acetate (2×30 mL). The combined organic phases were combined, dried (MgSO4), filtered and stripped. The volatiles were removed under reduced pressure. The residue was dissolved in DCM (6 mL) and treated with HCl (4.8 mL, 1M solution in dioxane) at rt. After stirring at rt for 90 min, the reaction mixture was concentrated to provide 78 mg (90%) of a brown oil. This material was dissolved in methanol (2 ml) to give a brown solution. DBU (61.0 mg, 60.4 µl, 401 µmol) was then added followed by ethyl 2-cyanoacetate (60.4 mg, 56.8 µl, 534 µmol). The reaction mixture was heated to 40° C. and stirred for 18 h. The reaction mixture was concentrated and purified by preparative TLC, eluting with 10% of methanol and 0.5% of ammonium hydroxide in DCM to provide 2 mg (2%) of the desired compound as a light brown oil. MS (M+H)+=324.

Example 9

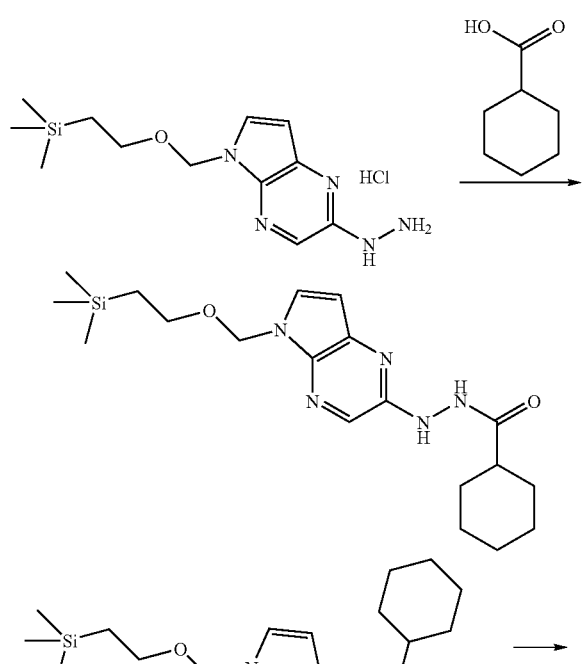

A flask containing a mixture of [5-(2-trimethylsilanyl-ethoxymethyl)-5H-pyrrolo[2,3-b]pyrazin-2-yl]-hydrazine hydrochloride (1.1 g, 3.48 mmol) and cyclohexane carboxylic acid (412 mg, 3.22 mmol) in dry dichloromethane (22 mL) was cooled to 0° C. (ice bath) under nitrogen atmosphere. To this cooled mixture was added triethylamine (0.9 mL, 7.27 mmol) and EDCI (703 mg, 3.68 mmol). After 30 minutes the cooling bath was removed and the material was stirred overnight at rt. A saturated aqueous solution of sodium bicarbonate (40 mL) and methylene chloride (40 mL) were added and the mixture was shaken in a separatory funnel. The organic phase was collected and washed with brine (40 mL). The aqueous phases were back extracted with methylene chloride (2×30 mL). The organic phases were combined, dried (MgSO4), filtered and stripped. The crude residue was purified by SiO2 chromatography eluting with a 35-60% ethyl acetate in hexanes gradient to afford 584 mg (54%) of compound X as a yellow solid. MS (M+H)+=390.

A solution of the hydrazide (578 mg, 1.48 mmol) in tetrahydrofuran (21 mL) and carbon tetrachloride (17 mL) was cooled to 0° C. (ice bath) under argon atmosphere. N,N-Diisopropylethylamine (2.6 mL, 14.8 mmol) was added followed by the addition of triethylethyl solution (8.9 mL, 1M in THF) via slow drop-wise addition over 5 minutes. The mixture was stirred to ambient temperature over night. After stirring at rt for 24 h, the reaction was cooled to 0° C. (ice bath) and treated with diisopropylethylamine (2.3 mL, 7.4 mmol) followed by triethylethyl solution (4.45 mL, 1M in THF). Water (40 mL) and ethyl acetate (40 mL) were added and the mixture was stirred vigorously for 10 minutes. The organic phase was collected and the aqueous phase was back extracted with ethyl acetate (2×30 mL). The combined organic phases were combined, dried (MgSO4), filtered and stripped. The crude residue was purified by SiO2 chromatography eluting with a 35-60% ethyl acetate in hexanes gradient to afford 450 mg (82%) of compound as a brown oil. MS (M+H)+=372.

Compound (225 mg, 0.606 mmol) was SEM de-protected under similar conditions to those described in Example 2 above. The crude residue was purified by SiO2 chromatography eluting with a 3-6% methanol in methylene chloride gradient to afford 110 mg (76%) of compound as a yellow solid. MS (M+H)+=242.

Example 10

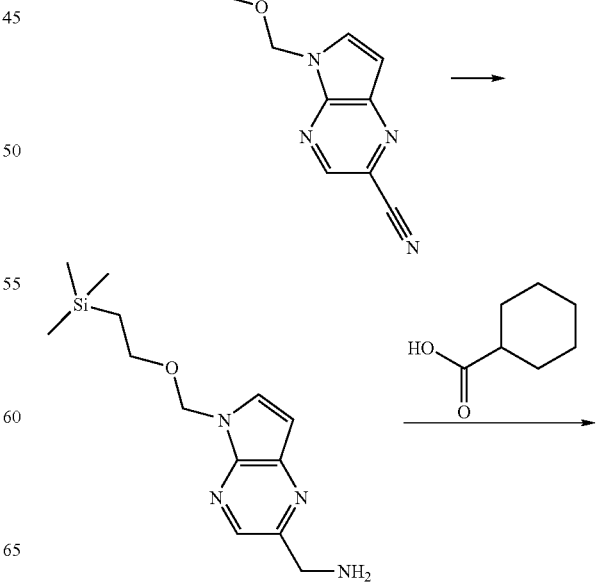

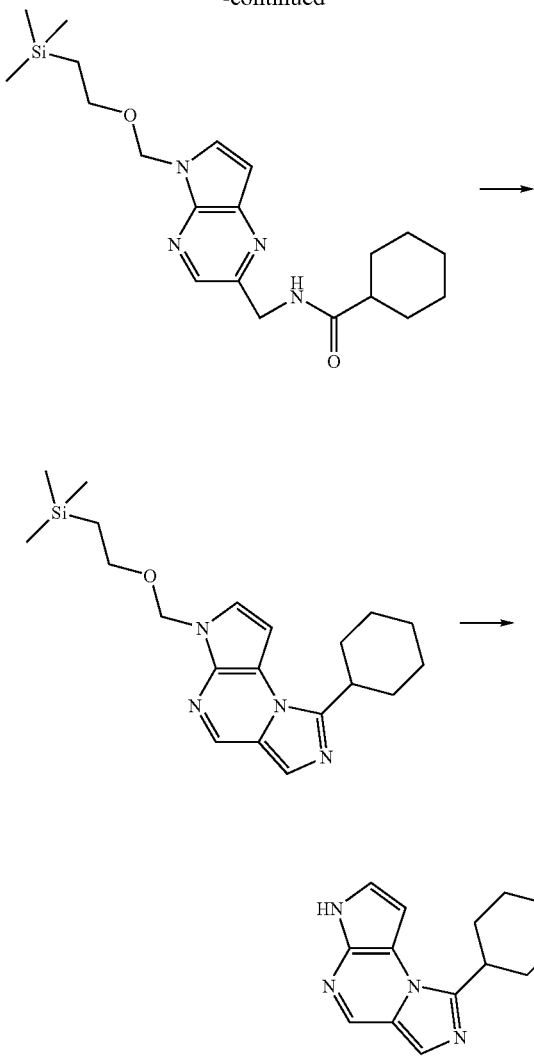

A mixture of pyrrolopyrazine (1.66 g, 5.06 mmol), CuI (342 mg, 1.8 mmol), K₄[Fe(CN)₆] (433 mg, 1.17 mmol) in 1-methyl-imidazole (5 mL) was stirred at 140° C. for 16 H. The reaction was cooled to rt and treated with ether (60 mL) and water (140 mL). The organic phase was separated and the aqueous was extracted with ether (40 mL). The combined organic extracts were washed with water (3×100 mL), dried with Na$_2$SO$_4$, and concentrated under reduced pressure to provide the desired compound 1.33 g (96%) as a light brown solid. MS (M+H)$^+$=275.

A solution of the cyanopyrazine (1.32 g, 4.8 mmol) in THF (20 mL) was cooled to 0° C. Lithium aluminum hydride (7.2 mL, 1M solution in THF) was slowly added. The reaction mixture was warmed to rt and stirred at that temperature for 2 h. The reaction was cooled to 0° C. and diluted with ether. The reaction was treated with water (1 mL) and aq. 15% NaOH (0.28 mL). The reaction stirred at rt for 15 min. The solids were removed by filtration and washed with ethyl acetate. The filtrate was evaporated under reduced pressure to provide 560 mg (42%) of the desired compound. MS (M+H)$^+$=278.

A flask containing a mixture of the amine (560 mg, 2.01 mmol) and cyclohexane carboxylic acid (2.28 μL, 2.02 mmol) in dry dichloromethane (17 mL) was cooled to 0° C. (ice bath) under nitrogen atmosphere. To this cooled mixture was added triethylamine (0.58 mL, 3.6 mmol), HOBT (361 mg, 2.65 mmol) and EDCI (499 mg, 2.34 mmol). After 30 minutes the cooling bath was removed and the material was stirred overnight at rt. An saturated aqueous solution of sodium bicarbonate (40 mL) and methylene chloride (40 mL) were added and the mixture was shaken in a reparatory funnel. The organic phase was collected and washed with brine (40 mL). The aqueous phases were back extracted with methylene chloride (2×30 mL). The organic phases were combined, dried (MgSO$_4$), filtered and evaporated under reduced pressure to provide 820 mg (54%) of the desired material. The crude mixture was taken to the next step without purification. MS (M+H)$^+$=389.

A solution SEM pyrrolopyrazine (820 mg, 0.464 mmol) in 15 mL of THF and 9 mL of carbon tetrachloride was cooled to 0° C. Diisopropylethyl amine (811 μL, 4.64 mmol) was added followed by slow addition of triethylphosphine (2.79 mL, 2.79 mmol) over five minutes. After warming to room temperature, reaction mixture was stirred over the weekend. Reaction mixture was poured into 90 mL of water and 90 mL of EtOAc and stirred for 20 min. Separated and aqueous was extracted with ethyl acetate, combined, dried with sodium sulfate, concentrated. LC/MS shows desired mass in ~17% purity. The crude material was carried to the next step without further purification. The crude material was treated with TBAF (8 mL, 1M solution in THF) and stirred at rt overnight. The reaction mixture was diluted with water and extracted with ethyl acetate. The organic extracts were dried over magnesium sulfate, filtered and concentrated. The crude product was purified by preparative TLC, eluting with ethyl acetate to provide 3 mg (2%) of the desired compound as a light brown oil. MS (M+H)$^+$=241.

JAK Assay Information

Determination of IC$_{50}$ of Janus Kinase (JAK) Inhibition:
  Enzymes and peptide substrate used are described below:
    JAK1: Recombinant human kinase domain from Invitrogen (Cat # PV4774)
    JAK3: Recombinant human kinase domain from Millipore (Cat # 14-629)
    JAK2: Recombinant human kinase domain from Millipore (Cat # 14-640)
    Substrate: N-terminally biotinylated 14-mer peptide derived from activation loop of JAK1 with sequence of the peptide substrate: Biotin-KAIETDKEYYTVKD (SEQ ID NO: 1)
  Assay conditions used are described below:
    Assay Buffer: JAK Kinase Buffer: 50 mM Hepes [pH 7.2], 10 mM MgCl$_2$, 1 mM DTT, 1 mg/ml BSA. The assay is carried out in this buffer.
    Assay Format: The kinase activity of all three JAK kinases is measured using a radioactive, end-point assay and with trace amounts of $^{33}$P-ATP. The assays are carried out in 96-well polypropylene plates.

Experimental Method:
  All concentrations are final in the reaction mixture and all incubations are carried at room temperature. Assay steps are described below:

Compounds are serially diluted in 100% DMSO typically at a 10× starting concentration of 1 mM. Final concentration of DMSO in the reaction is 10%.

Compounds are preincubated with enzyme (0.5 nM JAK3, 1 nM JAK2, 5 nM JAK1) for 10 minutes.

Reactions are initiated by the addition of a cocktail of the two substrates (ATP and peptide premixed in the JAK Kinase Buffer). In the JAK2/JAK3 assays, ATP and the peptide are used at concentrations of 1.5 uM and 50 uM, respectively. JAK1 assay is carried out at an ATP concentration of 10 uM and a peptide concentration of 50 uM. The duration of the assay for JAK2 and JAK3 is 20 minutes. JAK1 assay is carried out for 40 minutes. With all three enzymes, reactions are terminated by the addition of 0.5M EDTA to a final concentration of 100 mM.

25 ul of terminated reactions are transferred to 150 ul of a 7.5% (v/v) slurry of streptavidin-coated sepharose beads in $MgCl_2$- and $CaCl_2$-free 1× Phosphate Buffered Saline containing 50 mM of EDTA in 96-well, 1.2 um Multi-Screen-BV filter plates. After a 30-minute incubation, the beads are washed under vacuum with the following buffers:

3 to 4 washes with 200 ul of 2M NaCl.
3 to 4 washes with 200 ul of 2M NaCl plus 1% (v/v) phosphoric acid.
1 wash with water.

Washed plates are dried in a 60° C. oven for between 1 to 2 hours.

70 ul of Microscint 20 scintillation fluid is added to each well of filter plates and after at least 30 minutes of incubation, radioactive counts are measured in a Perkin Elmer microplate scintillation counter.

Representative $IC_{50}$ results are in Table II below:

TABLE II

| Compound | Ic50 h-jak3 baculovirus-c:no additive | Ki h-jak3 baculovirus-c:no additive |
| --- | --- | --- |
| I-2 | 0.02023 | 0.01038 |
| I-3 | 0.039945 | 0.02049 |
| I-4 | 0.069295 | 0.000964 |
| I-5 | 0.20276 | 0.11873 |
| I-6 | 0.06929 | 0.03555 |
| I-7 | 0.231445 | 0.10255 |
| I-8 | 0.44914 | 0.22457 |
| I-9 | 0.024998 | 0.01282 |
| I-10 | 0.09298 | 0.04769 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula I

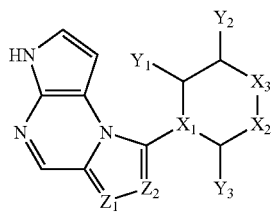

wherein:
$Z^1$ is CH;
$Z^2$ is CH or N;
$X^1$ is CH or N;
$X^2$ is $CH_2$, $NS(=O)_2R^1$, or $NC(=O)R^{1'}$;
  $R^1$ is lower alkyl;
  $R^{1'}$ is H, amino, or $R^{1''}$;
    $R^{1''}$ is lower alkyl, optionally substituted with one or more $R^{1'''}$;
      $R^{1'''}$ is halogen, lower alkoxy, cyano, or amino;
$X^3$ is $CHR^2$ or $S(=O)_2$;
  $R^2$ is H or lower alkyl;
$Y^1$ is H, lower alkyl, lower alkoxy, halogen, or lower haloalkyl;
$Y^2$ is H or lower alkyl; and
$Y^3$ is H, lower alkyl, lower alkoxy, halogen, or lower haloalkyl;
or a pharmaceutically acceptable salt thereof.

2. The compound of claim 1, wherein $Z^1$ is CH and $Z^2$ is CH.

3. The compound of claim 2, wherein $X^1$ is CH.

4. The compound of claim 2, wherein $X^1$ is N.

5. The compound of claim 3, wherein $X^3$ is $S(=O)_2$.

6. The compound of claim 3, wherein $X^3$ is $CH_2$.

7. The compound of claim 6, wherein $X^2$ is $NS(=O)_2CH_2CH_3$.

8. The compound of claim 7, wherein $Y^2$ is H and $Y^3$ is H.

9. The compound of claim 8, wherein $Y^1$ is methyl.

10. The compound of claim 1, wherein $Z^1$ is CH and $Z^2$ is N.

11. The compound of claim 10, wherein $Y^2$ is H and $X^3$ is $CH_2$.

12. The compound of claim 11, wherein $X^2$ is $NS(=O)_2CH_2CH_3$.

13. The compound of claim 12, wherein $Y^1$ is methyl.

14. The compound of claim 11, wherein $Y^1$ is H and $X^2$ is $CH_2$.

15. The compound of claim 14, wherein $Y^3$ is methyl.

16. The compound of claim 1 selected from the group consisting of:
  8-(1,1-Dioxo-1$\lambda^6$-thiomorpholin-4-yl)-3H-3,4,8a-triaza-as-indacene;
  8-Cyclohexyl-3H-3,4,8a-triaza-as-indacene;
  8-(2-Methyl-piperidin-1-yl)-3H-3,4,8a-triaza-as-indacene;
  8-((3S,4S)-1-Ethanesulfonyl-4-methyl-piperidin-3-yl)-3H-3,4,8a-triaza-as-indacene;
  8-((3S,4R)-1-Ethanesulfonyl-4-methyl-piperidin-3-yl)-3H-3,4,8a-triaza-as-indacene;
  1-((1R,2S)-2-Methyl-cyclohexyl)-6H-2,3,5,6,8b-pentaaza-as-indacene;
  1-((3R,4R)-1-Ethanesulfonyl-4-methyl-piperidin-3-yl)-6H-2,3,5,6,8b-pentaaza-as-indacene;
  1-Cyclohexyl-6H-2,3,5,6,8b-pentaaza-as-indacene;
  3-[(3S,4S)-4-Methyl-3-(6H-2,3,5,6,8b-pentaaza-as-indacen-1-yl)-piperidin-1-yl]-3-oxo-propionitrile; and
  1-Cyclohexyl-6H-2,5,6,8b-tetraaza-as-indacene.

17. A compound of Formula II

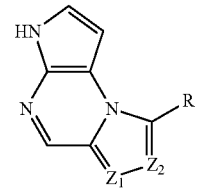

wherein:
$Z^1$ is CH;
$Z^2$ is CH or N;
R is cycloalkyl or heterocycloalkyl, optionally substituted with one more $R^1$; and
  $R^1$ is lower alkyl, halogen, lower haloalkyl, lower alkoxy, lower alkylsulfonyl, or $C(=O)R^2$;
  $R^2$ is H, amino, or $R^3$;
    $R^3$ is lower alkyl, optionally substituted with one or more $R^4$; and
    $R^4$ is halogen, lower alkoxy, cyano, or amino;
or a pharmaceutically acceptable salt thereof.

18. A pharmaceutical composition comprising the compound of claim 17, admixed with at least one pharmaceutically acceptable carrier, excipient or diluent.

19. The pharmaceutical composition of claim 18, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

* * * * *

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Synthetic

<400> SEQUENCE: 1

Lys Ala Ile Glu Thr Asp Lys Glu Tyr Tyr Thr Val Lys Asp
1               5                   10
```